(12) United States Patent
Metzger et al.

(10) Patent No.: US 7,541,602 B2
(45) Date of Patent: Jun. 2, 2009

(54) SYSTEM AND METHOD FOR NONINVASIVELY MONITORING CONDITIONS OF A SUBJECT

(75) Inventors: Yaacov Metzger, Hod Hasharon (IL); Michal Rokni, Zichron Ya'akov (IL); Revital Pery-Shechter, Rishon Lezion (IL)

(73) Assignee: Or-Nim Medical Ltd., Lod (IL)

( * ) Notice: Subject to any disclaimer, the term of this patent is extended or adjusted under 35 U.S.C. 154(b) by 179 days.

(21) Appl. No.: 11/757,698

(22) Filed: Jun. 4, 2007

(65) Prior Publication Data

US 2008/0296514 A1 Dec. 4, 2008

(51) Int. Cl.
*A61B 5/05* (2006.01)
(52) U.S. Cl. .............. 250/494.1; 250/493.1; 600/310; 600/322; 600/473; 600/474; 600/330; 600/407
(58) Field of Classification Search ............ None
See application file for complete search history.

(56) References Cited

U.S. PATENT DOCUMENTS

| | | | |
|---|---|---|---|
| 5,738,635 A | 4/1998 | Chapelon et al. | |
| 6,738,653 B1 * | 5/2004 | Sfez et al. ........ | 600/322 |
| 6,802,812 B1 * | 10/2004 | Walker et al. ...... | 600/309 |
| 6,815,694 B2 * | 11/2004 | Sfez et al. ........ | 250/492.1 |
| 6,957,096 B2 * | 10/2005 | Sfez et al. ........ | 600/407 |
| 2002/0067269 A1 | 6/2002 | Cadell et al. | |
| 2003/0018246 A1 | 1/2003 | Govari et al. | |
| 2006/0122475 A1 | 6/2006 | Balberg et al. | |
| 2006/0247506 A1 | 11/2006 | Balberg et al. | |

OTHER PUBLICATIONS

D. M. Hueber et al: "Non-invasive and quantitative near-infrared haemoglobin spectrometry in the piglet brain during hypotoxic stress, using a frequency-domain multidistance instrument", Phys. Med. Biol. 46 (2001)41-62.
A. Lev et al: "In vivo demonstration of the ultrasound-modulated light technique", J. Opt. Soc. Am. A vol. 20, No. 12 (Dec. 2003).
G. Yu et al: "Time-dependable blood flow and oxygenation in human skeletal muscles measured with noninvasive near-infrared diffuse optical spectroscopies", Journal of Biomedical Optics 10:2 Mar./Apr. 2005, 024027-1/024027-12.

* cited by examiner

*Primary Examiner*—David A. Vanore
(74) *Attorney, Agent, or Firm*—Browdy and Neimark, P.L.L.C.

(57) ABSTRACT

A method and system are presented for use in determining one or more parameters of a subject. A region of interest of the subject is irradiated with acoustic tagging radiation, which comprises at least one acoustic tagging beam. At least a portion of the region of interest is irradiated with at least one electromagnetic beam of a predetermined frequency range. Electromagnetic radiation response of the at least portion of the region of interest is detected and measured data indicative thereof is generated. The detected response comprises electromagnetic radiation tagged by the acoustic radiation. This enables processing of the measured data indicative of the detected electromagnetic radiation response to determine at least one parameter of the subject in a region corresponding to the locations in the medium at which the electromagnetic radiation has been tagged by the acoustic radiation, and outputting data indicative of the at least one determined parameter.

46 Claims, 13 Drawing Sheets

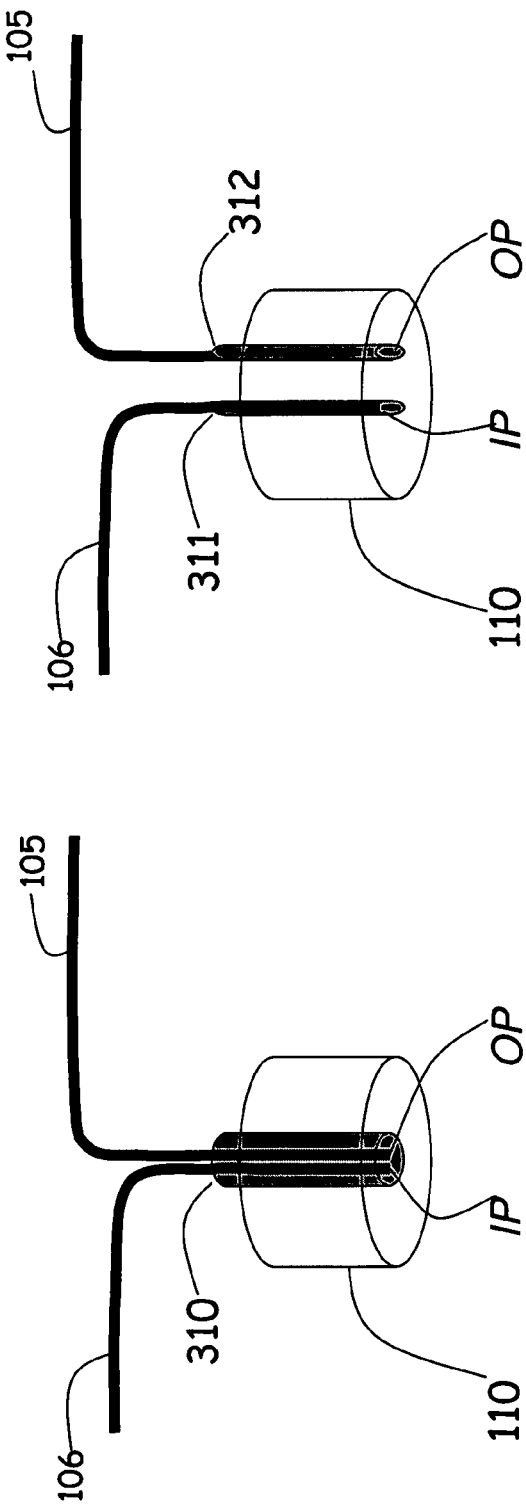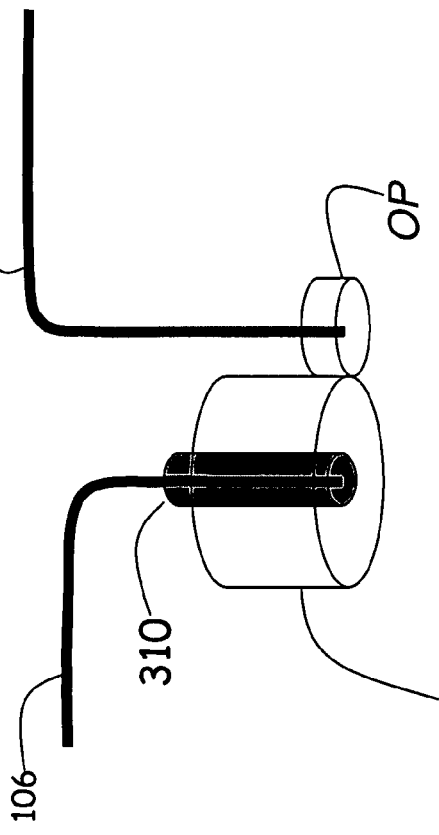

SYSTEM AND METHOD FOR NONINVASIVELY MONITORING CONDITIONS OF A SUBJECT

FIELD OF THE INVENTION

This invention relates to a method and system for monitoring a subject's condition, based on scattered light distribution through turbid media. The invention is particularly useful in medical applications.

BACKGROUND OF THE INVENTION

Non invasive monitoring and imaging using non-ionizing radiation, allows medical professionals to diagnose and monitor a patient without invasive surgeries, or even without drawing blood. Pulse oximetry is one such revolutionizing technology, where non invasive monitoring of blood oxygenation using light has replaced blood gas analysis. Thus, pulse oximetry has become a gold standard monitor in every clinical setting, and has saved millions of lives.

During non-invasive monitoring, the concentration of certain chromophores (such as oxygenated and deoxygenated hemoglobin in oximetry) is calculated by detecting light that escapes the tissue, determining the optical properties of the tissue, and deriving therefrom the concentrations of the chromophores. Providing the tissue is homogenous, simple models allow for the calculation of these concentrations. However, as biological tissue is a complex scattering medium, measuring the local optical properties becomes a challenging task.

As light is highly scattered while propagating through turbid media such as biological tissue, photons that escape the tissue and reach a detector do not provide information about the path that they followed as they propagated through the medium. To acquire information about the optical properties of the tissue in the photons' path, several methods and algorithms have been developed. Such methods include frequency-domain spectroscopy, and photoacoustic spectroscopy [D M Hueber et al Phys. Med. Biol. 46 (2001) 41-62].

SUMMARY OF THE INVENTION

The present invention utilizes the principles of ultrasound tagging of light. More specifically, the tagging of light by acoustic radiation is used to determine the optical response of a region of interest. The invention may be used, for example, to significantly improve oximetry and pulse oximetry based measurements.

According to the invention, a region of interest in a subject (e.g. human body) is illuminated with at least one wavelength of light, and is irradiated with acoustic radiation (preferably ultrasound) such that the acoustic radiation overlaps the illuminated region in at least a part of the region of interest during the duration of illumination and/or detection of the illuminating light (this overlapping volume is termed "tagged volume"). This acoustic radiation is termed acoustic tagging radiation. Light scattered from the subject's body and including photons that are tagged by the acoustic radiation and those that are not, is appropriately detected.

It is a common goal of any optical measurement technique to be capable of providing a high resolution measurement of the local light distribution with an improved signal to noise ratio (SNR). The present invention addresses this problem by providing a novel method and system based on the principles of acoustic tagging of light, where the acoustic radiation is appropriately modulated (coded) to provide high-resolution and high-SNR measurement results.

The main idea of the present invention is based on the following understanding: The effect termed "Ultrasound Tagging of Light" (UTL) is based on the interaction of acoustic waves with the same tissue volume that is being probed by light. This interaction causes the light wave to be modulated, or tagged, with the characteristics of the acoustic wave (i.e. frequency, phase). As the propagation of acoustic waves in tissue is relatively slow (about 1500 m/sec in soft tissue), the location of the interaction of light with the acoustic radiation can be determined. The efficiency and power of the interaction of the acoustic waves with the medium affects the spatial and temporal resolution and the SNR of the measurement. There are three possible modalities for the generation of acoustic waves, a continuous wave (CW), a short burst of waves (SB), and a pulse. Operation with continuous waves produces a higher SNR. When a continuous acoustic wave (at a predetermined frequency range) interacts with light, and light is collected throughout the full propagation of the acoustic waves, a higher acoustic energy is available for the interaction, thereby increasing the signal. In addition, the spectral bandwidth of the continuous acoustic wave can be very narrow, thus reducing noise bandwidth. Thereby the SNR is greatly improved. However, the spatial resolution of a measurement produced with continuous acoustic waves is not as high as a measurement produced with short bursts or pulses of acoustic waves. This reduced spatial resolution is particularly limiting when the measurement geometry calls for propagation of acoustic waves essentially parallel to the direction of light propagation. As for the use of short bursts of waves and pulses, this provides better spatial resolution, but the acoustic energy of the interaction is lower and the bandwidth is wider as compared to those of a continuous wave mode, resulting in reduced SNR.

There is accordingly a need in the art for a measurement technique which can achieve both high spatial resolution and high SNR. The present invention solves this problem by utilizing generation of continuous acoustic waves (and therefore improving the SNR), where the continuous acoustic wave is a modulated (coded) signal characterized by a narrow autocorrelation function, thereby improving the spatial resolution.

The expression "narrow autocorrelation function" refers to autocorrelation which is negligible for any delay time larger than the determined time resolution of the system. The latter may for example be determined as the time resolution of detection of the electromagnetic radiation response, or as the temporal bandwidth of the acoustic excitation of the ultrasound transducer, or as the required spatial resolution divided by the speed of sound in the media.

In some embodiments of the invention, a pseudo random sequence, or specially designed sequences such as Barker codes, or Golay codes (used in radar technology) can be used. A combination of several such arbitrary signals (having different phases and/or amplitudes) can be used interchangeably. According to one specific but not limiting example, the modulated signal may be a non-periodic time function with predefined time intervals between such non-periodic occurrences.

In some embodiments of the present invention, the coding comprises a series of short pulses with high amplitude, that are separated by periods of low amplitude (or even zero amplitude). The duration of the high amplitude pulses depends on the required time resolution of the system. The separation duration between two consecutive pulses is determined such that the phase of light propagating through the media during the second pulse is independent of the phase of light during the previous pulse of acoustic radiation. In addition, the consecutive high amplitude pulses may differ in frequency or may also be chirped.

The present invention thus provides for a 3D mapping of the light distribution in a turbid medium, obtaining a non invasive means for collecting data about the structure and composition of the turbid medium. The use of a continuous acoustic signal utilizes the acoustic and light energy more efficiently, and lower acoustic and optical signals can be used while maintaining the desired SNR. Thus, the light levels and acoustic levels introduced into the subject are safer.

According to one broad aspect of the invention, a method is provided for use in determining one or more parameters of a subject's tissue, the method comprising:

(a) irradiating a region of interest of the subject with acoustic tagging radiation, the acoustic tagging radiation comprising at least one acoustic tagging beam being a coded continuous acoustic wave in the form of a predetermined function of at least one parameter of the acoustic radiation varying over time during a measurement time interval, said predetermined time function having a narrow autocorrelation;

(b) irradiating at least a portion of the region of interest with at least one electromagnetic beam of a predetermined frequency range;

(c) detecting an electromagnetic radiation response of said at least portion of the region of interest and generating data indicative thereof, said response comprising electromagnetic radiation tagged by the acoustic radiation, thereby enabling processing said data indicative of the detected electromagnetic radiation response, to determine at least one parameter of the subject's tissue in a region corresponding to the locations in the medium at which the electromagnetic radiation has been tagged by the acoustic radiation, and output data indicative of the at least one determined parameter.

According to another broad aspect of the invention, there is provided a system for use in determining one or more parameters of a subject, the system comprising:

an acoustic unit configured and operable for irradiating a region of interest with acoustic tagging radiation comprising at least one acoustic tagging beam being a coded continuous acoustic wave in the form of a predetermined function of at least one parameter of the acoustic radiation varying over time during a predetermined time interval used for measurements, said predetermined function having narrow autocorrelation; and an optical unit configured and operable for irradiating at least a portion of the region of interest with at least one electromagnetic beam of a predetermined frequency range, detecting an electromagnetic radiation response of said at least portion of the region of interest and generating data indicative thereof, said response comprising electromagnetic radiation tagged by the acoustic radiation, said data being indicative of the at least one parameter of the subject in a region corresponding to the locations in the medium at which the electromagnetic radiation has been tagged by the acoustic radiation.

The generation of such a coded acoustic wave can be implemented as follows:

An arbitrary sequence can be produced and stored, the arbitrary sequence activating an arbitrary waveform generator. The latter (or an appropriate arbitrary switch) thus generates an arbitrary sequence of electronic signals which corresponds to the stored arbitrary sequence. Such an electronic signal in the form of an arbitrary sequence presents a modulating or coding signal for operating an acoustic transducer. The output of the acoustic transducer thus generated is a corresponding modulated acoustic wave. The arbitrary sequence used for generation of a modulating signal can incorporate modulations of the original signal in frequency and/or phase and/or amplitude and/or any other parametric domain. The modulated signal should have a narrow autocorrelation that defines the time resolution of the detection. As indicated above, this may be a pseudo random sequence, or specially designed sequences (such as Barker codes, or Golay codes used in radar technology), or a combination of several such arbitrary signals having different phases and/or amplitudes used interchangeably.

The detection of the light response of the medium is implemented using one or more appropriate photodetectors, each for receiving light returned (scattered) from the medium and generating an electronic output corresponding to the detected light intensity. Light collected by the detector includes both tagged and untagged photons. The electronic output signal of the detector is processed by correlating it with the original modulated signal (stored arbitrary sequence).

According to some embodiments of the present invention, the correlation is done using a cross correlation function to determine the optical properties of the medium at different depths. To this end, the cross correlation is determined for different time delays from the onset of the acoustic wave. At each delay, the cross correlation represents the intensity of tagged light corresponding to a distance from the acoustic transducer (e.g. depth in the subject) equal to the product of the speed of sound in the subject's tissue and the delay time. Since the process of acoustic tagging of light does not have a constant phase relation with the acoustic tagging signal, a phase matching mechanism is preferably added to the cross correlating algorithm. The amplitude of the cross correlation at each delay is assumed to correspond to a function of the light distribution at the corresponding depth and the pressure amplitude of the acoustic wave at that depth. For example, this function corresponds to the product of the two parameters. The light distribution can be determined by eliminating the contribution of the acoustic wave distribution to the amplitude of the cross correlation. By fitting the light distribution to an expected distribution (for example, an exponential attenuation), the optical properties of the layer where the amplitude of the cross correlation is measured are determined.

In some embodiments of the present invention, multiple light sources and/or detectors and/or acoustic sources may be used. Such configurations improve the spatial resolution of the measurements and enable the mapping of a larger volume of the medium. For the purposes of the present invention, when multiple acoustic sources (i.e. multiple acoustic waves) are used, all acoustic sources can use either different frequency ranges or the same frequency range, as long as the modulating sequences of the different acoustic sources have zero or near zero cross correlation. When the electromagnetic response signal is detected and decoded, each acoustic beam tagging effect can be estimated separately by correlating the respective received signal with the original modulating sequence for this acoustic source. The contribution of other acoustic sources to such a correlation is negligible given the zero or near zero cross correlation between the sequences, as will be described below.

When multiple acoustic sources are used, they may be arranged and operated such that acoustic radiations produced by these sources interfere in at least a volume part of the region of interest. By this, the acoustic power in that volume can be enhanced or nullified according to the desired application. In this case, the different acoustic signals generated by different acoustic sources are selected such as to provide non-zero cross correlation thereof at a predetermined delay.

Thus, in the region of interest, the overall acoustic radiation is a combination of several acoustic signals.

The present invention can be used for various applications, including medical and non-medical ones. Considering the medical applications, the present invention can be used for example for determining oxygen saturation in blood and/or tissue, as well as determining concentration of substance(s) in blood and/or tissue such as hemoglobin, glucose, etc. As an example, the invention is used in the determination of oxygen saturation of the tissue layers, and is therefore described below with respect to this specific application, but it should be understood that the invention is not limited to this specific application.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 3A shows a segment of an exemplary signal, FIG. 3B shows auto correlation of said signal, and FIG. 3C shows the correlation $C(\tau_0)$ for time delay $\tau_0 = 10^{-5}$ seconds;

FIGS. 6A-6C and 7A-7B show examples of different configurations of a probe device according to the invention.

DETAILED DESCRIPTION OF EXEMPLARY EMBODIMENTS

Figure 1:
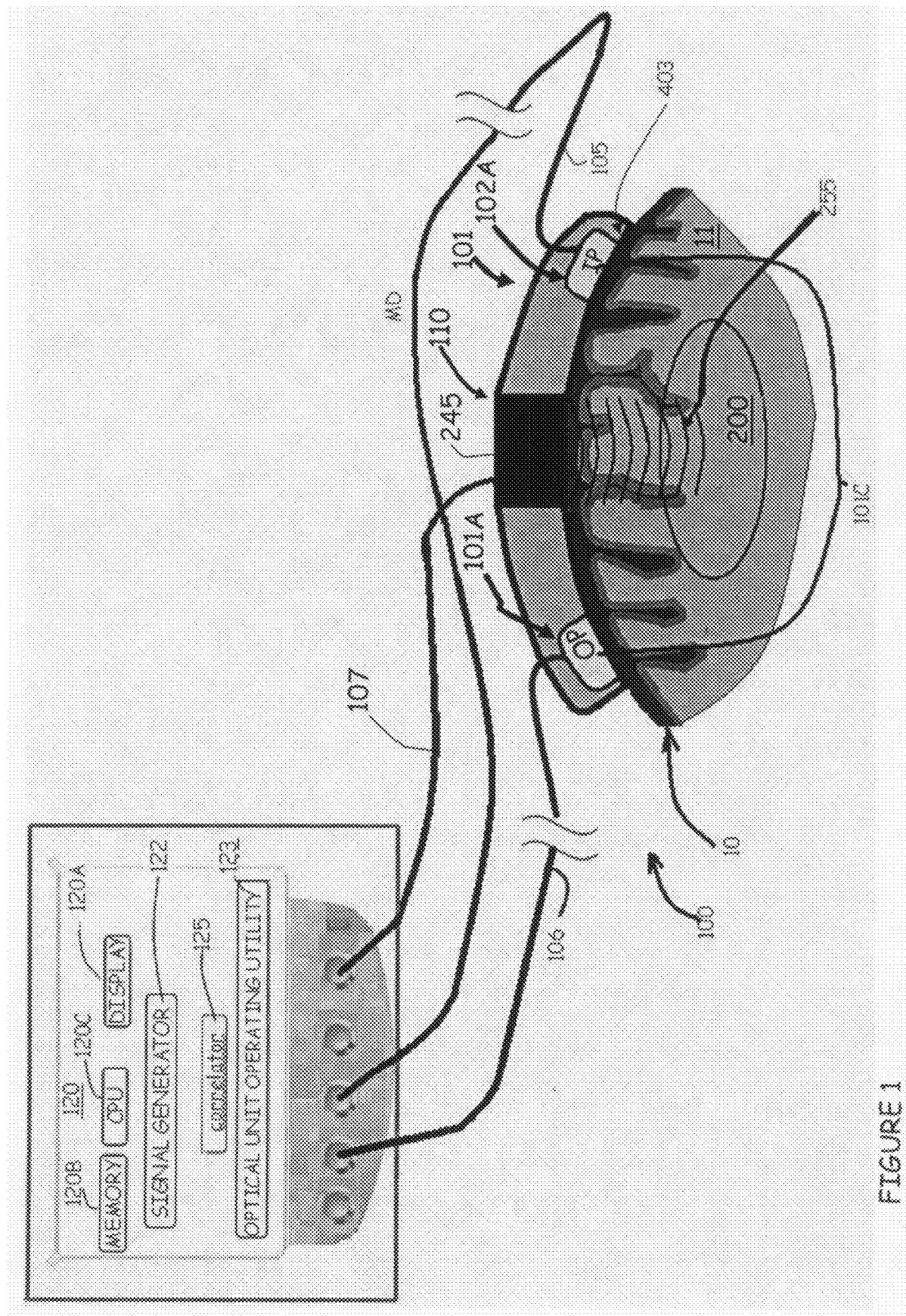
FIG. 1 is a schematic illustration of a measurement system according to an embodiment of the present invention.

Reference is made to FIG. 1 illustrating schematically a specific but not limiting example of a measurement system, generally designated 100, configured and operable according to the invention for non-invasive determination of one or more parameters (properties of tissue components) of a subject, particularly a human or animal body. The parameter(s) to be determined may include oxygen saturation level, or values/levels of various other parameters such as the concentration of an analyte in the patient's blood, or the perfusion of an analyte/metabolite in tissues. The values of these parameters are derived from the light distribution in a region of interest 200 as will be described below.

System 100 includes such main constructional parts as a measurement unit 101 and a control unit 120. Measurement unit 101 includes an optical or electromagnetic unit (module) 101C and an acoustic unit (module) 110. Optical module 101C includes an illumination assembly 101A and a light detection assembly 102A, and acoustic module 110 is configured as an acoustic transducer arrangement including one or more acoustic transducers. Control unit 120 is configured to control the operation of measurement unit 101, and to process, analyze measured data generated by measurement unit 101 (its detection assembly), and display the results of the analysis.

Illumination assembly 101A includes one or more illumination sources associated with one or more different locations with respect to the region of interest. Similarly, detection assembly 102A includes one or more detector units associated with one or more different detecting locations. It should be noted that the illumination source includes one or more lighting elements each formed, for example, by a light emitter and possibly also a light guiding unit (e.g., an optical fiber or fiber bundle). For example, a probe part of the measurement unit by which it is to be brought to the body part under measurements may carry the light emitter itself, or may carry a distal end of a light guiding unit which by its opposite end is connected to an external light emitter. The detector unit includes one or more light detecting elements each formed by a light sensor and possibly also a light guiding unit (e.g., optical fiber or fiber bundle); the probe part by which the measurement unit is to be brought to the body part may carry the light sensor or a distal end of the light guide which by its opposite end is coupled to an external light sensor.

The lighting element(s) and/or detecting element(s) may be incorporated within the acoustic transducer arrangement as will be described further below with reference to FIGS. 6A-6C and 7A-7B. The lighting element(s) and detecting element(s) may be incorporated in one unit and the acoustic transducer arrangement placed to the side of (and not in between) the detector element(s) and the lighting element(s).

In the example of FIG. 1, illumination assembly 101A includes a single illumination unit, and light detection assembly 102A includes a single detector unit. It should be understood that this does not necessarily signify the use of a single lighting element and/or a single detecting element. Such a single illumination unit, as well as a single detection unit, may include an array of lighting elements and an array of detecting elements, such that all the lighting elements of the same illumination unit are associated with the same location with respect to the region of interest, and similarly all the detecting elements of the same detection unit are associated with the same location relative to the region of interest. In some other embodiments of the invention, the illumination assembly includes more than one illumination unit and/or more than one detection unit, as will be described below.

Optical module 101C and acoustic module 110 are connected to control unit 120, e.g., by cables 105, 106 and 107 as shown in FIG. 1, or using wireless signal transmission (e.g. IR, RF or acoustic signal transmission) as the case may be.

Control unit 120 is typically a computerized system including inter alia a power supply unit (not shown); a control panel with input/output functions (not shown); a data presentation utility (e.g. display) 120A; a memory utility 120B; and a data processing and analyzing utility (e.g. CPU) 120C. Also provided in control unit 120 are a signal generator utility 122 (e.g. function generator and phase control) configured and operable to control the operation of acoustic unit (transducer arrangement) 110, and an appropriate utility 123 configured for operating optical unit 101C. Data processing and analyzing utility 120C is preprogrammed for receiving measured data (MD) coming from detection assembly 102A (via cable 105 in the present example) and for processing this measured data to identify the detected light distribution corresponding to measurements locations in the region of interest, thereby enabling determination of one or more desired parameters of the region of interest, e.g., oxygen saturation level. Also provided in the control unit is a correlator utility 125 (typically a software utility) associated with the signal generator 122.

According to this example, measurement unit 101 is configured as a probe having a support structure (preferably flexible) 403 to be put in contact with the body part to be measured. Support structure 403 carries at least part of illumination assembly 101A and at least part of detection assembly 102A. As shown in the figure, provided on the probe are: a light output port OP (constituting a lighting element) associated with the illumination source, a light input port IP (constituting a detecting element) associated with the detector unit, and an acoustic port 245 associated with the acoustic unit. It should be understood that light output port OP may be integral with the light emitting element(s) or may be constituted by the distal end of an optical fiber unit connected at its other end to one or more light emitting element(s) located outside the support structure (e.g., at the control unit). Similarly, light input port IP may be integral with the light detecting element(s) or may be constituted by the distal end of an optical fiber unit which by its other end is connected to one or more detecting elements (light sensors) located outside the support structure (e.g., at the control unit).

Generally, illumination assembly 101A can be configured to produce light of at least one wavelength. According to an embodiment of the present invention, the illumination assembly generates light of multiple (at least two) different wavelengths. Illumination assembly 101A may for example be preprogrammed to produce the different wavelength components at different times, or to simultaneously produce wavelength components with different frequency- and/or phase-modulation. Accordingly, control unit 120 is preprogrammed to identify, in a signal generated by detection assembly 102A, the corresponding wavelength of light, using time, and/or phase, and/or frequency analysis. The detection assembly may include an appropriate frequency filter.

Thus, illumination assembly 101A may include the light emitter(s) carried by support structure 403 and communicating with control unit 120 (using cables 106 or wireless signal transmission). Alternatively, the light emitter(s) may be located outside support structure 403 (e.g., within control unit 120) and connection 106 is constituted by a light guiding assembly (e.g., optical fibers) for guiding light to light output port OP located on support structure 403. Detection assembly 102A includes one or more light detectors such as a photomultiplier tube, photodiode or an avalanche photodiode. The light detector may include an image pixel array, e.g., CCD or other array of photodiodes. The detector(s) may be accommodated outside support structure (probe) 403, e.g., may be located within control unit 120, and returned light (light response) may be guided from input port IP of the detection assembly via light guiding means 105 (e.g., optical fibers). Alternatively, the detector(s) may be located at the support structure and connection 105 is configured to connect an electrical output of the detector(s) indicative of measured data MD to control unit 120. As indicated above, detection assembly 102A may include two separate detectors or an array of detectors. It should also be understood that connections 105 and 106 may be electric wires connecting control unit 120 to the illumination assembly and detection assembly located on support structure, 403, or the connection may be wireless.

Thus, generally, the terms "illumination assembly" and "detection assembly" as carried by a support structure (probe) which is brought to a body part to be measured, are constituted by at least light transmitting and receiving ports. Similarly, transducer arrangement 110 may be located on support structure 403 (so as to be brought in acoustic contact with the skin), and connected to control unit 120 (its signal generator 122 and CPU 120C) using cables and/or optical fibers 107 and/or using wireless means. Alternatively, connection 107 may constitute an acoustic guiding unit for connecting the transducer(s) located outside the support structure (e.g., at the control unit) to acoustic output port 245 on the support structure.

Transducer arrangement 110 may be a single acoustic element, configured and operable for emitting focused or unfocused acoustic beams or for emitting acoustic pulses; or a piezoelectric phased array capable of producing acoustic beams with variable direction, focus, duration and phase; or may be an array of silicon units or other pressure generating units configured as a single element or an array of elements (phased array); or a complete ultrasound imaging probe comprising transmitting and receiving units. The transducer arrangement may be connected to an amplifier (not shown), e.g. located within control unit 120, operable to amplify electronic signals generated by signal generator 122. The control unit is preprogrammed to operate transducer arrangement 110 (via signal generator 122) in a predetermined manner to produce a coded acoustic continuous wave, which is a predetermined function of at least one parameter of the acoustic radiation varying over time during a measurement time interval. This predetermined function is selected to have a narrow autocorrelation function (i.e. an autocorrelation which is negligible for any delay time larger than the determined time resolution of the system, for example, determined as the time resolution of detection of the electromagnetic radiation response, or as the temporal bandwidth of the ultrasound transducer, or as the required spatial resolution divided by the speed of sound in the media), as will be described more specifically below.

Detection assembly 102A generates electronic signals in response to the amplitude and phase of light collected at input port IP. These electronic signals may be filtered by analog and/or digital filters, for example bandpass filters, that are appropriately provided being connected to data processing utility 120C of control unit 120 or being a part of this processing utility.

Figure 2A:
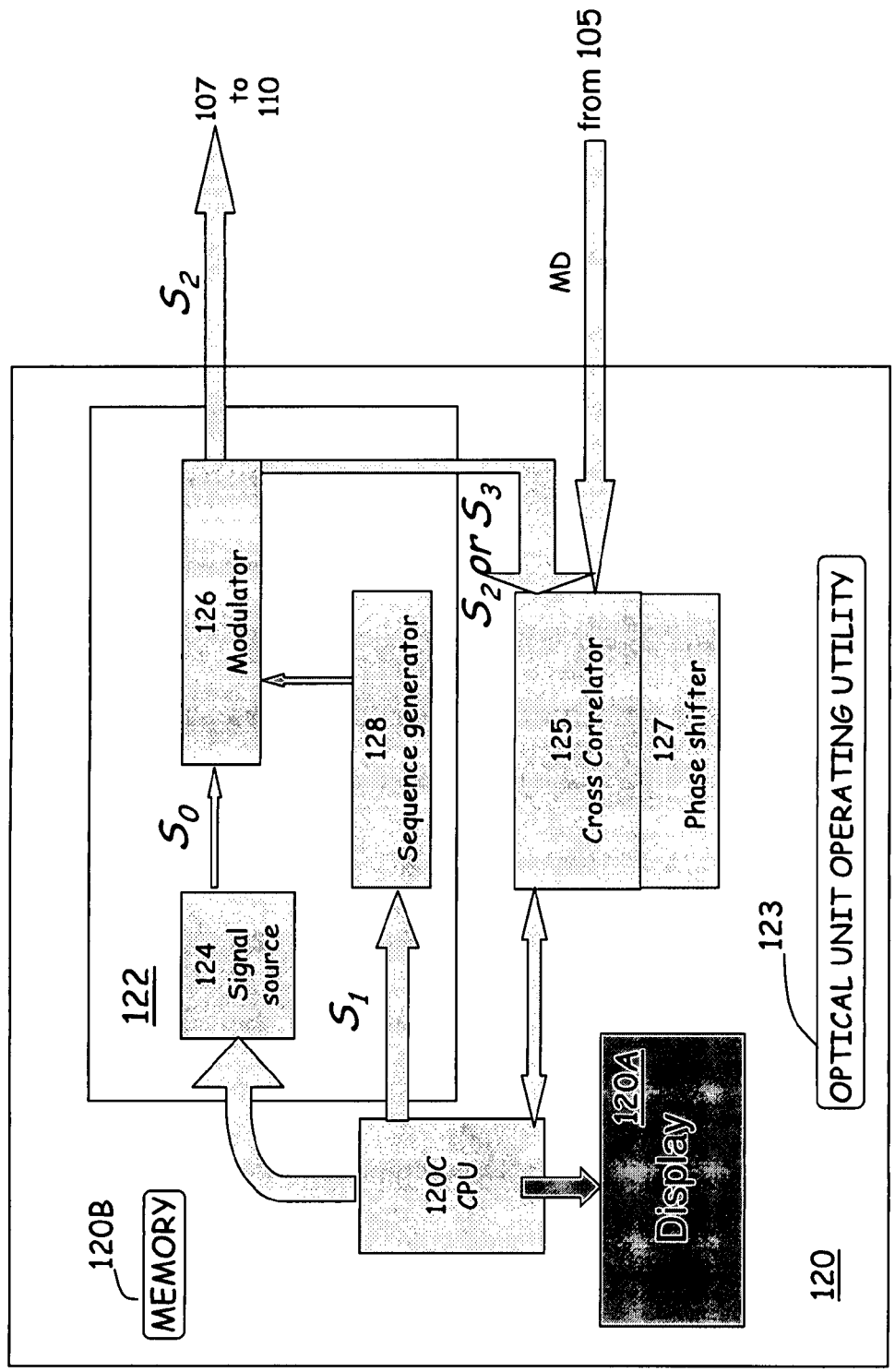
FIG. 2A is a block diagram of an example of a control unit for use in the system of the present invention.

Reference is now made to FIG. 2A showing more specifically an example of the functional elements and operation of control unit 120. As shown, signal generator 122 includes a signal source 124, a modulator 126 and a sequence generator 128. Also, in the present example, the control unit includes a phase shifter utility 127, as in the present example phase is a modulatable parameter in a continuous acoustic wave to be generated by the acoustic unit. However, the invention is not limited to this specific example, and the control unit may include a frequency and/or amplitude shifter utility, alternatively or additionally to the phase shifter. CPU 120C controls the operation of signal generator 122 and cross correlator 125, and receives signals from cross correlator 125. CPU 120C also controls signal source 124 and sequence generator 128. Signal source 124 generates a base signal $S_0$ (e.g. a sine wave of a certain frequency, or a chirped signal, or a train of square waves at a central frequency). Signal $S_0$ passes through modulator 126 that controls one or more of its parameters (e.g. at least one of the following: phase, frequency, frequency gradient (chirp), phase jump, amplitude, duty cycle, chirp gradient) to produce a modulating (or coding) signal $S_2$ to operate the acoustic transducer to produce an acoustic (ultrasound) sequence. Alternatively modulating signal $S_2$ comprises a combination of such sequences. The operation of modulator 126 is controlled by sequence generator 128. CPU 120C transmits a signal $S_1$ to sequence generator 128, that controls its operation. Sequence generator 128 in turn controls the operation of modulator 126 according to this signal $S_1$. Modulating signal $S_2$ that exits modulator 126 is a result of the combination of base signal $S_0$ with the modulation induced by modulator 128 on this signal. This signal $S_2$ is transmitted to transducer arrangement 110 via connection 107. An additional power amplifier can be used to amplify signal $S_2$ before actuating the transducer. Signal $S_2$ is also transmitted to cross correlator 125, which correlates this signal $S_2$ with measured data MD coming from detection unit 102A through connection 105. Alternatively, cross correlator 125 may correlate a signal $S_3$ corresponding to signal $S_2$ with the measured data. Corresponding signal $S_3$ is for example the amplitude of signal $S_2$ or its absolute value, or another function corresponding to signal $S_2$. Phase shifter 127 controls the phase of signal $S_3$, such that a phase shift is generated between signal $S_2$ and signal $S_3$. The output of cross correlator 125 (e.g. the amplitude or phase of the cross correlation at different delays) is processed by CPU 120C and displayed on display 120A.

Figure 2B:
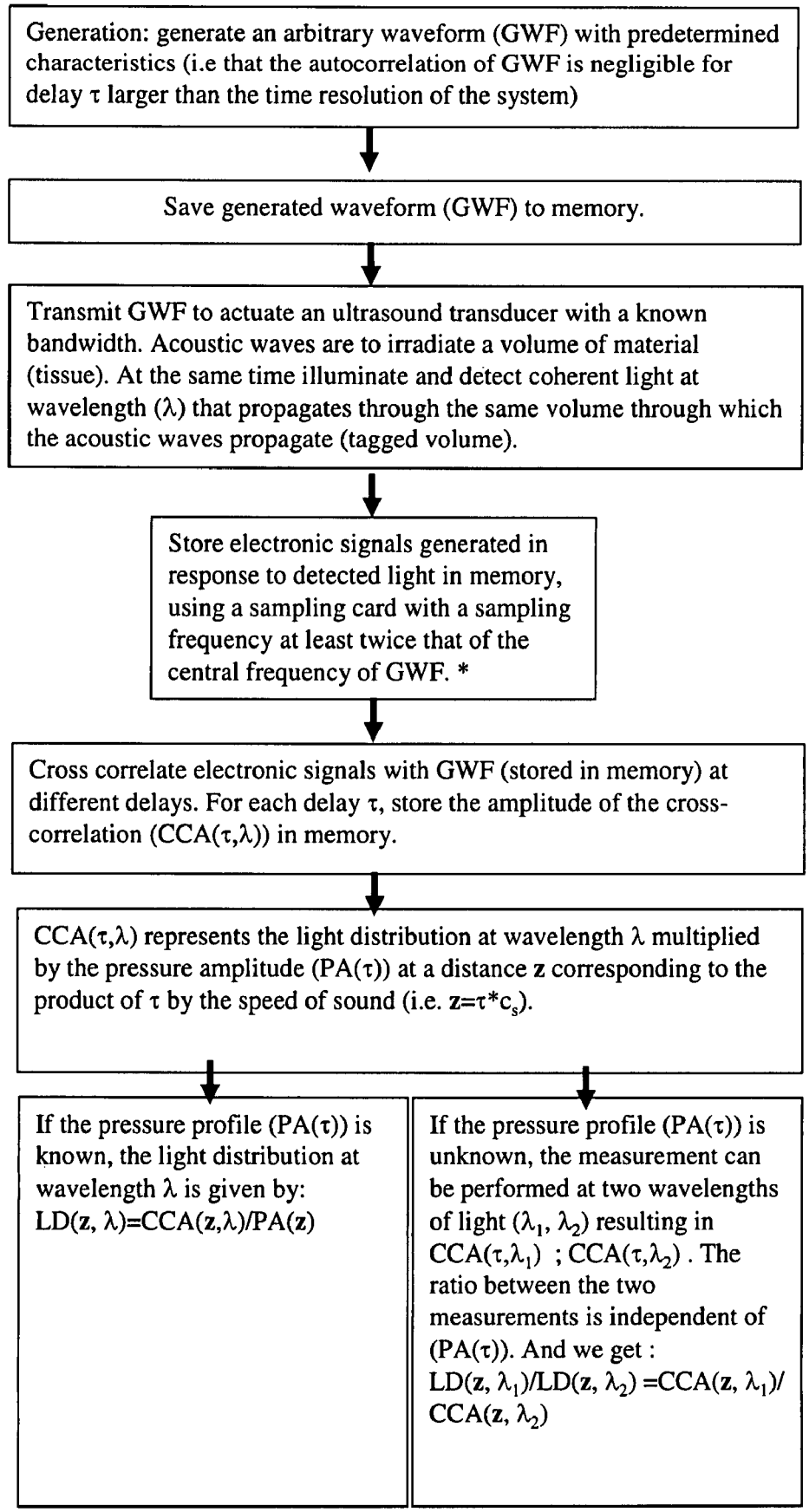
FIG. 2B is a flow chart of an example of a method of the present invention.

Reference is made to FIG. 2B exemplifying a method of the present invention suitable to be used to extract the light distribution in the tissue. An arbitrary waveform (GWF) is generated with predetermined characteristics such that the auto-correlation of GWF is negligible for any delay r larger than the time resolution of the system. This waveform GWF is saved to memory. This arbitrary waveform corresponds to the above-described modulating signal $S_2$.

The GWF is transmitted to actuate an ultrasound transducer (110 in FIG. 1) with a known bandwidth, for producing acoustic waves in the form of a non-periodic sequence to irradiate a volume of medium (tissue), at least part of a region of interest (200 in FIG. 1). Concurrently, the illumination assembly is operated to illuminate the medium with coherent light of a certain wavelength $\lambda$. This light propagates through the same volume through which the acoustic waves propagate (tagged volume), and light returned from the medium is detected (representing a light response of the medium).

Electronic signals generated by the detection assembly in response to the detected light are stored in memory, using a sampling card with a sampling frequency, which is at least twice the transducer's bandwidth, thereby enabling exact reconstruction of a continuous-time signal from its samples. These signals are cross correlated against the GWF electronic signals, or against a function of the GWF signal as described below, stored in memory with different time delays as applied. For each delay $\tau$, the amplitude of the cross-correlation (CCA($\tau,\lambda$)) is stored in memory. According to a preferred embodiment of the present invention, CCA($\tau,\lambda$) represents the light distribution at wavelength $\lambda$ multiplied by the acoustic power distribution or pressure amplitude, or a function of the acoustic pressure amplitude (PA($\tau$)) at a distance z corresponding to the product of $\tau$ and the speed of sound $c_s$ in the measured tissue (i.e. $z=\tau \cdot c_s$).

Pressure profile (PA($\tau$)) may or may not be known. In the case where the overall output light distribution function is a product of the pressure profile and the light distribution function within the medium, if the pressure profile is known, the light distribution LD at wavelength $\lambda$ is determined as $$LD(z,\lambda) = CCA(z,\lambda)/PA(z) \quad [1]$$

In case the (PA($\tau$)) is unknown, the measurements are performed using at least two different wavelengths $\lambda_1, \lambda_2$ of light providing two corresponding cross-correlation amplitudes CCA ($z, \lambda_1$) and CCA ($z, \lambda_2$) respectively. A ratio between the two measurements is independent of (PA($\tau$)), thus providing the ratio between the light distributions determined as $$\frac{LD(z,\lambda_1)}{LD(z,\lambda_2)} = \frac{CCA(z,\lambda_1)}{CCA(z,\lambda_2)}. \quad [2]$$

This will be described more specifically further below.

An example of an acoustic sequence used in an embodiment of this invention utilizes a random number generator with a long enough period (infinite relative to the used segment). An example of such a function might be:

$$S_2 = A_1 \cos(\omega t + \Theta(i)) \quad [3]$$

where $A_1$ is the amplitude, i=floor(t/$\tau$) and $\Theta$ is a sequence of random numbers in the range [0,2$\pi$] generated by any rectangular pseudo random generator.

In this example, the phase of signal $S_2$ of angular frequency $\omega$ (produced by modulator 126 in FIG. 2A) is randomly shifted for each segment of duration $\tau$. Here, $\tau$ determines the width of the auto correlation of the signal around zero, and hence the spatial resolution of the processed signal. The lowest limit of a range of values of $\tau$ may be bound by the bandwidth of the acoustic system, which is proportional to 1/$\tau$.

Figure 3A:
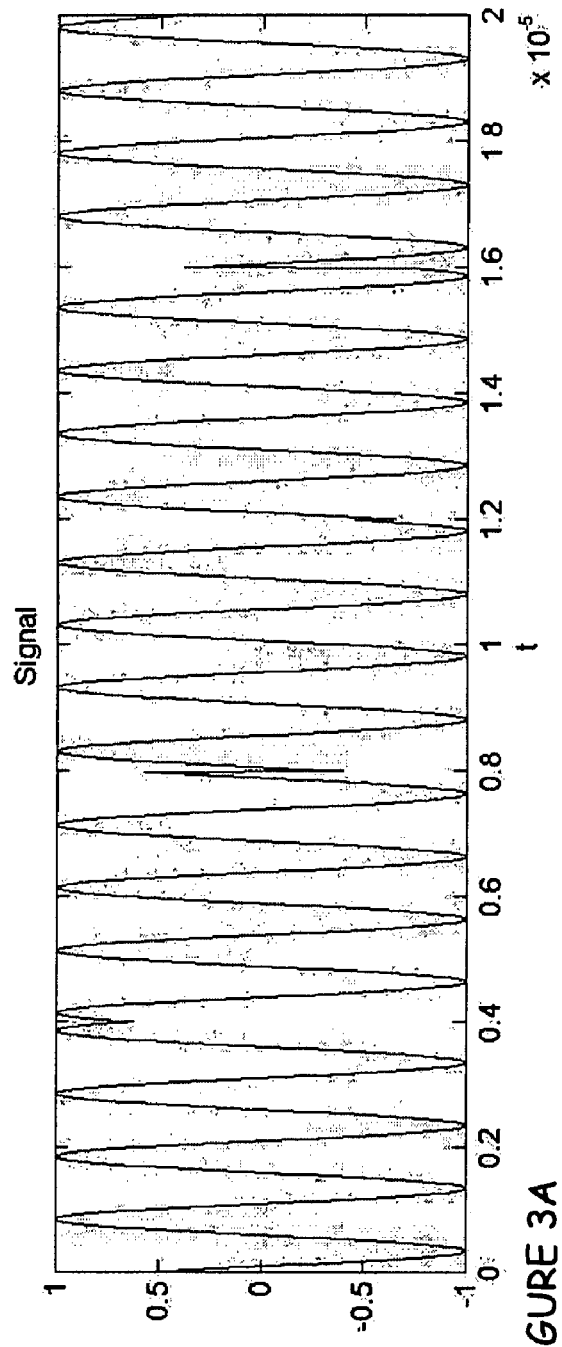
FIGS. 3A to 3C exemplify generation of a phase coded continuous acoustic signal, where
Figure 3B:
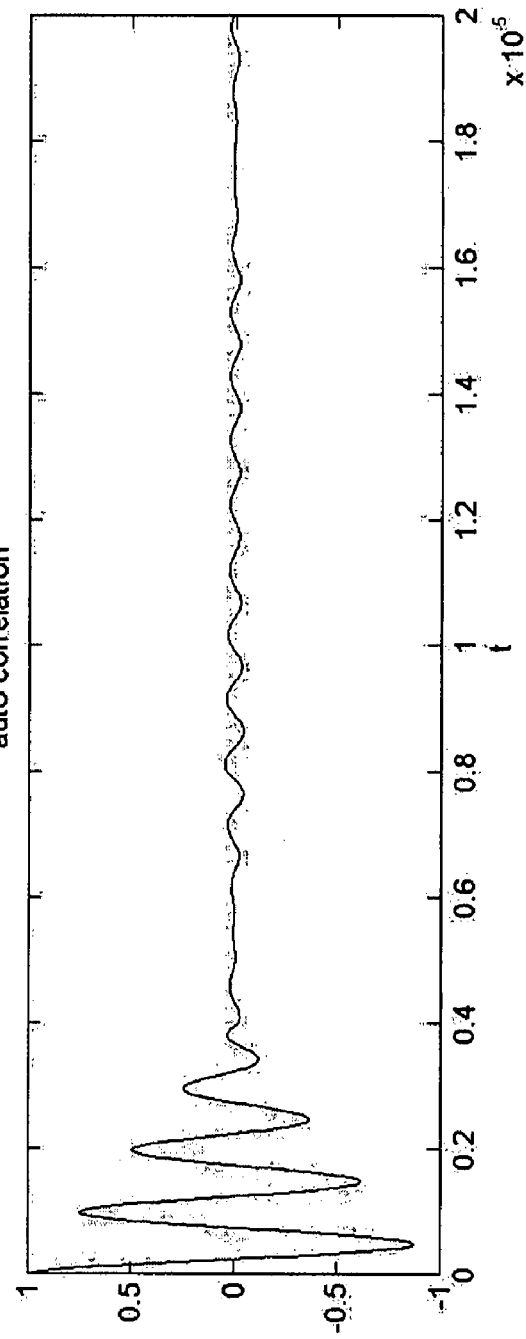

FIGS. 3A and 3B show, respectively, a segment of typical signal $S_2$ and its auto correlation. The tagging of incident light is detected as a result of interaction between acoustic waves and photons whose optical path and consequently phase is modulated by motion of scattering particles in the tissue. The phase of the received signal (corresponding to the tagged photons) relative to the phase of transmitted signal $S_2$ varies with time and depth and is also unknown.

Hence, processing of the measured data indicative of the detected light response includes processing of the correlated signal to search for the phase shift that gives the best correlation for each delay. This can be done by correlating the measured data with a complex phasor representation of the acoustic sequence and taking the absolute value of the resulting phasor. Considering the above example for signal $S_2$, the complex phasor is $S_p = e^{j\omega t + \Theta(i)}$ and the correlation C($\tau$) is to be calculated as $$C(\tau) = \sum_t D(t) S_p(t-\tau) \quad [4]$$

where D is the measured data (MD in FIG. 1); $S_p$ is an example for signals $S_3$ that can be used to determine the correlation between $S_2$ and the measured data.

If the signal originates from a known delay $\tau_0$ with arbitrary phase shift $\phi$, the result would be:

$$C(\tau_0) = \left| \sum_t \cos(\omega t + \Theta(i) + \phi) S_p(t-\tau_0) \right| \quad [5]$$

Figure 3C:
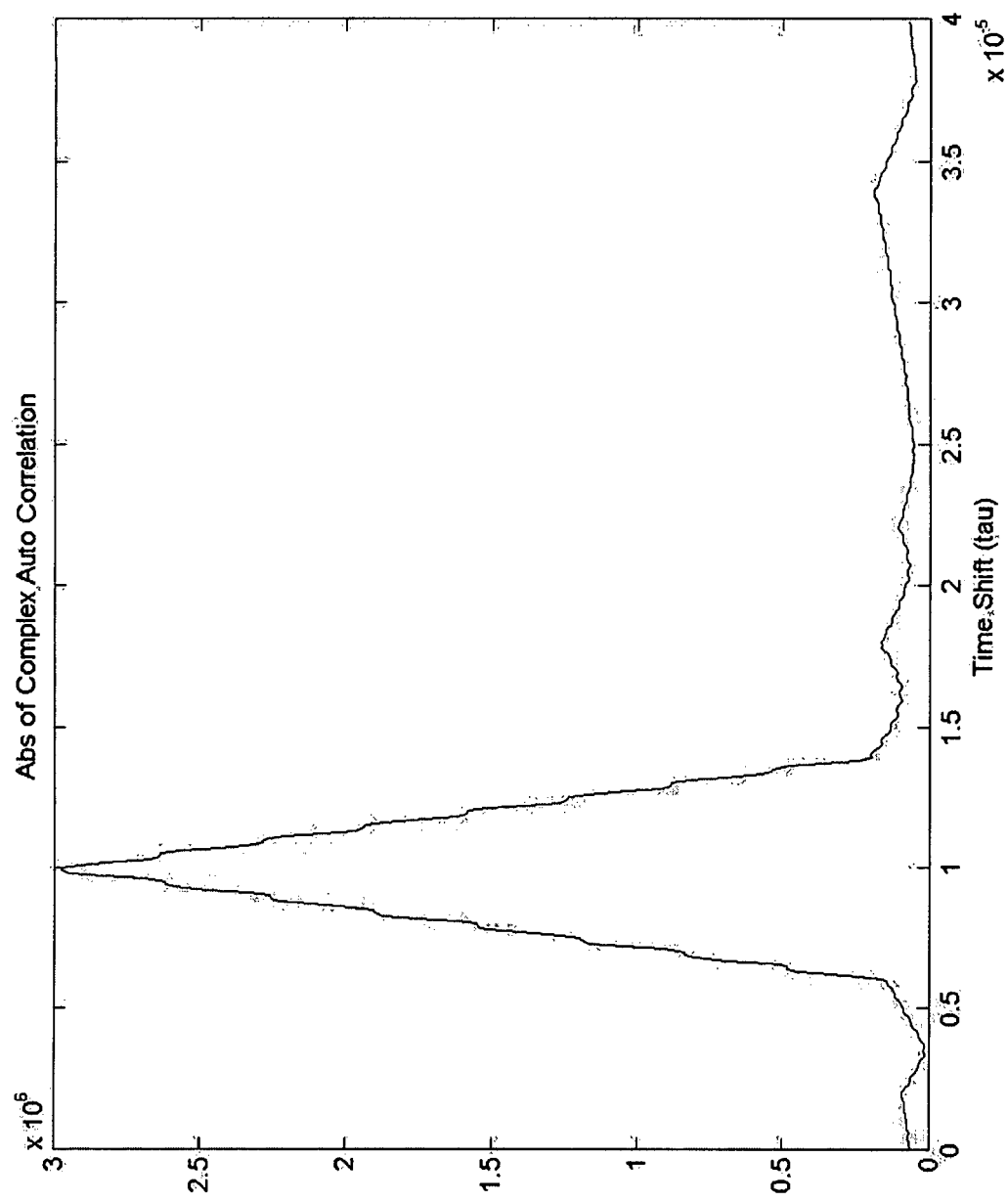

FIG. 3C illustrates the output C($\tau_0$) for $\tau_0 = 10^{-5}$ seconds and any value of $\phi$.

A measurement interval, i.e. the duration of signal $S_2$ in one measurement epoch, should preferably be as long as possible to enhance the signal to noise ratio (SNR) of the system. This can be implemented under the assumption that a scattering pattern is constant during the measurement, and therefore a phase relation of the measured data and the original signal $S_2$ is constant (even if such a relation is unknown). The temperature related Brownian motion of the scattering particles and other effects in a live tissue, such as motion of blood cells, enforce a practical upper limit for the measurement duration. These motions cause the interference pattern between the different photons on the sensing surface of a detector (called "speckle pattern") to be time varying, and cause the phase relation between the measured data and signal $S_2$ to vary with time. The measurement interval is therefore bounded by the speckle correlation time, defined, for example, as disclosed in Lev et al. in J. Opt. Soc. Am. A Vol. 20, No. 12 (December 2003).

Signal $S_2$ may comprise a sequence of short pulses, that are separated by periods of low (or even zero) amplitude. The separation period between pulses is determined as the time period where the phase of light that propagates through the media during the second pulse is independent of the phase of light that propagates through the media during the first pulse. Preferably, the separation time should be longer than the speckle correlation time. As the speckle correlation time depends on the properties of the media (such as its temperature), the signal $S_2$ can be determined according to the properties of the media being monitored. By another option, a plurality of separation durations can be used, and an optimal separation duration (providing optimal SNR or an optimized signal parameter) should be selected for measurement. According to yet another option, the optimal separation itself may be monitored, to provide a measure for a property of the media (such as its temperature or the flow of blood through the tissue).

In some cases, the above pulses can be replaced each by a set of multiple pulses that are transmitted over the same phase of light—thus to allow obtaining strong enough signal by means of averaging. The separation durations between these inner-set of pulses is selected to be large enough so that during the propagation of a single pulse (including echoes) through the region of interest the pulses do not co-exist inside the region of interest, and to be smaller than the speckle correlation time.

If longer integration is required to further improve the SNR, averaging can be carried out between separate measurements' intervals, but this averaging is done after the absolute value of the complex correlation is calculated separately for each of the measurements. In the case where $S_2$ comprises a series of pulses, the averaging may be performed over the absolute value of the cross correlation for each pulse separately. For example, averaging can be performed over a predetermined number of measurements that are separated by a predetermined time delay. This averaging might be advantageous in cases where the measured data is periodic (i.e. changes periodically as a function of time as in the case of modulation of the blood volume). For example, averaging over different portions of measured data can be correlated with the peaks/troughs of the blood volume during systolic/diastolic periods in a pulsating blood volume, having a predetermined delay from each other. In this case, a difference between the signals corresponds to the oxygen saturation levels of blood (as in the case of pulse oximetry).

Signal $S_2$ can for example include a plurality of different arbitrary signals. These may for example be different signals having different amplitudes and/or different frequencies and/or different phase variations.

The above example demonstrates random modulation of the phase of signal $S_2$. As indicated above, other parameters of signal $S_2$ may be modulated according to a predetermined function.

The following is an example related to a frequency modulation of signal $S_2$. Signal $S_2$ can be expressed by $$S_2 = \cos(\phi(t)), \quad [6]$$

where $\phi$ is selected so that $$\frac{d\phi}{dt} = \omega_i,$$

and where $i=\text{floor}(t/\tau)$ and $\omega$ is a random sequence with a square distribution in the assigned angular frequency range.

Figure 4A:
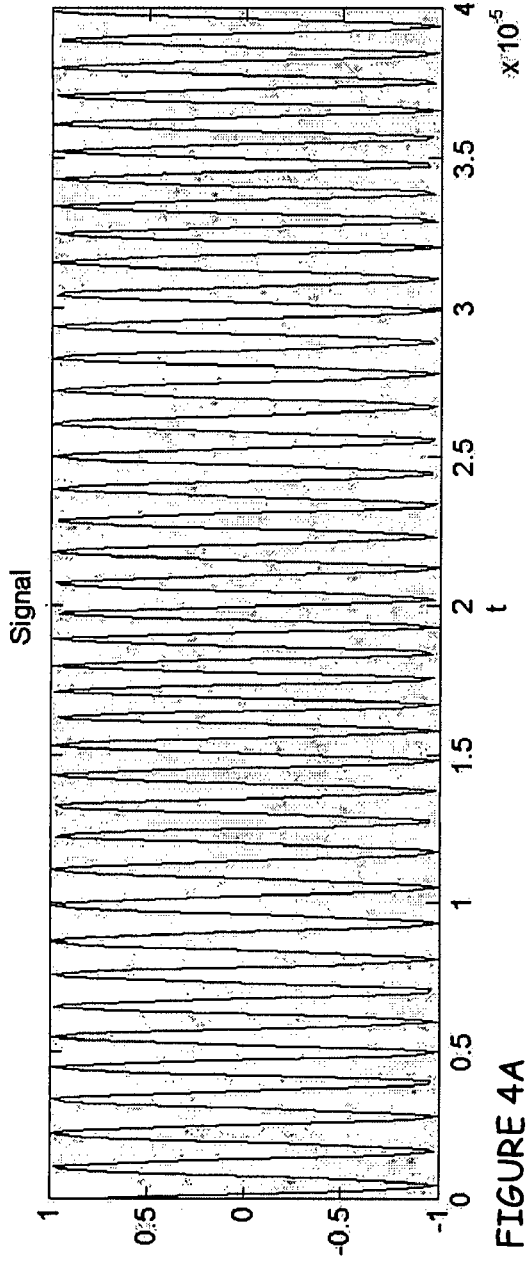
FIGS. 4A to 4C similarly show an example of generation of a frequency coded continuous acoustic signal.
Figure 4B:
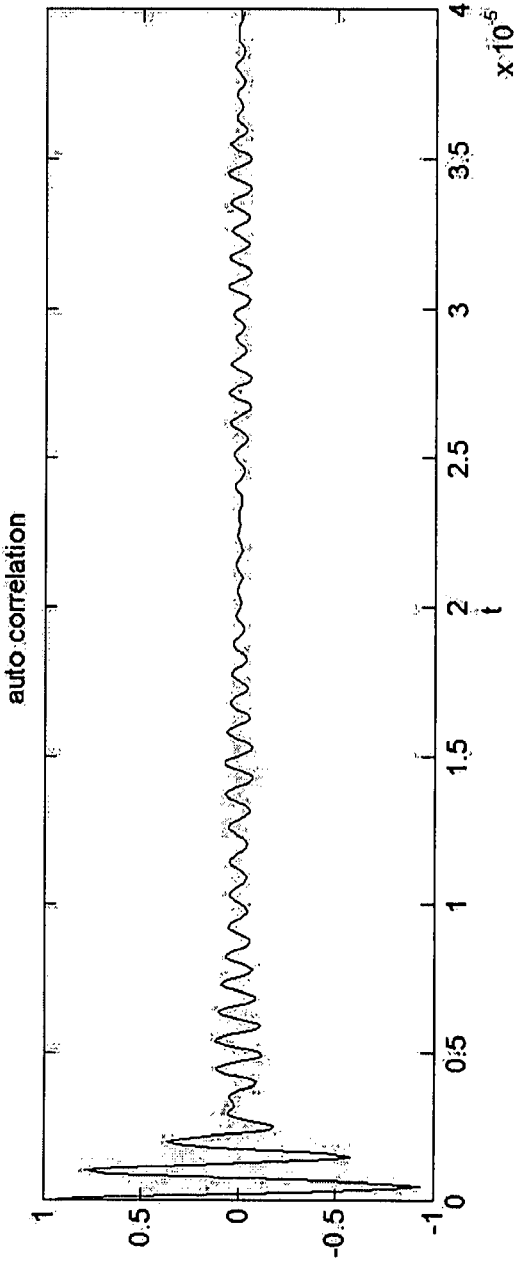
Figure 4C:
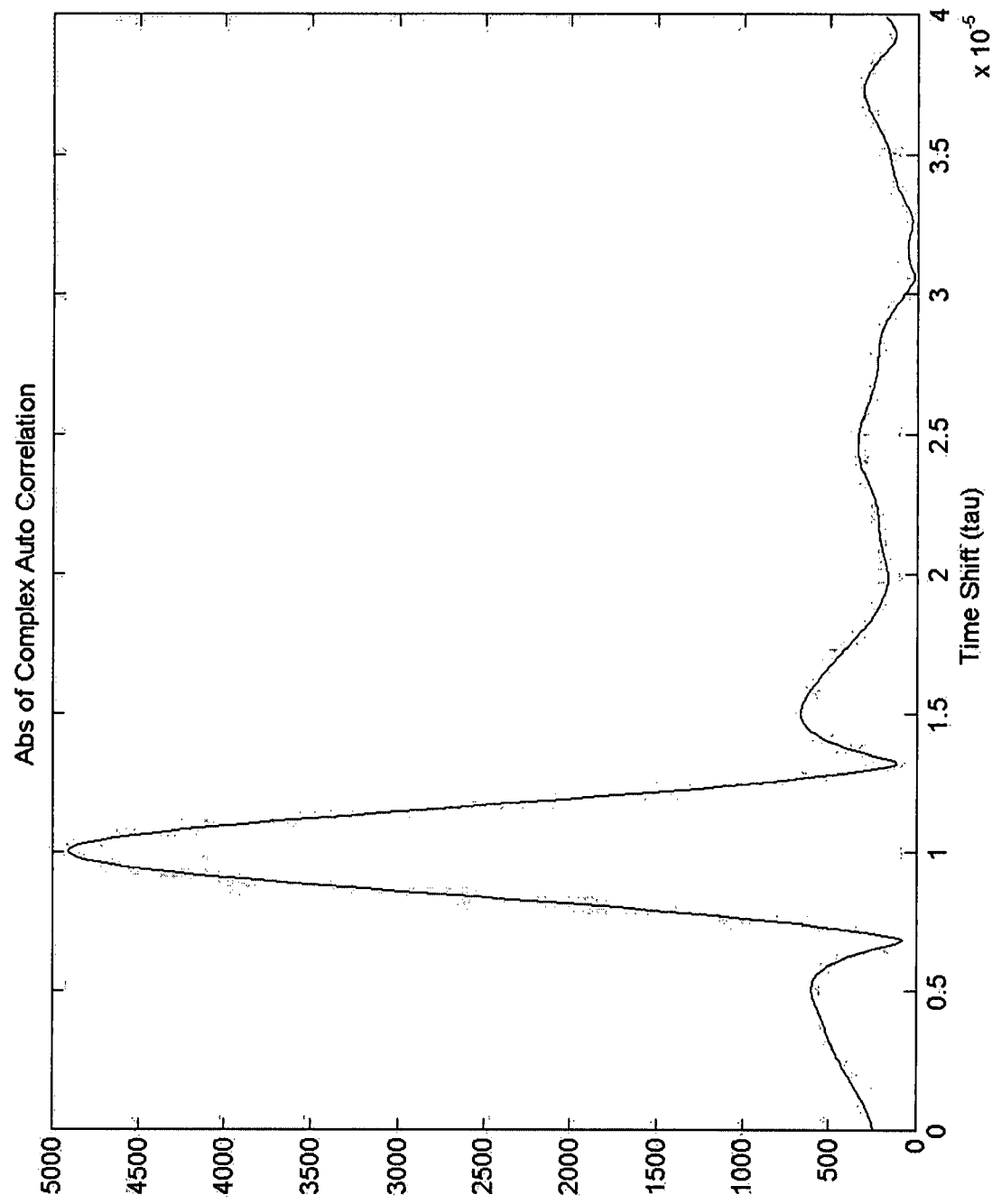

FIGS. 4A and 4B exemplify, respectively, a segment of signal $S_2$ and its autocorrelation. FIG. 4C shows the cross correlation $C(\tau)$ defined similarly to the above example for phase modulation.

It should be noted that the above description for cross correlation is based on digital signal processing. However, dedicated analog circuits that perform cross correlation with variable delays can be designed and constructed to provide a similar functional operation of the system.

Figure 5:
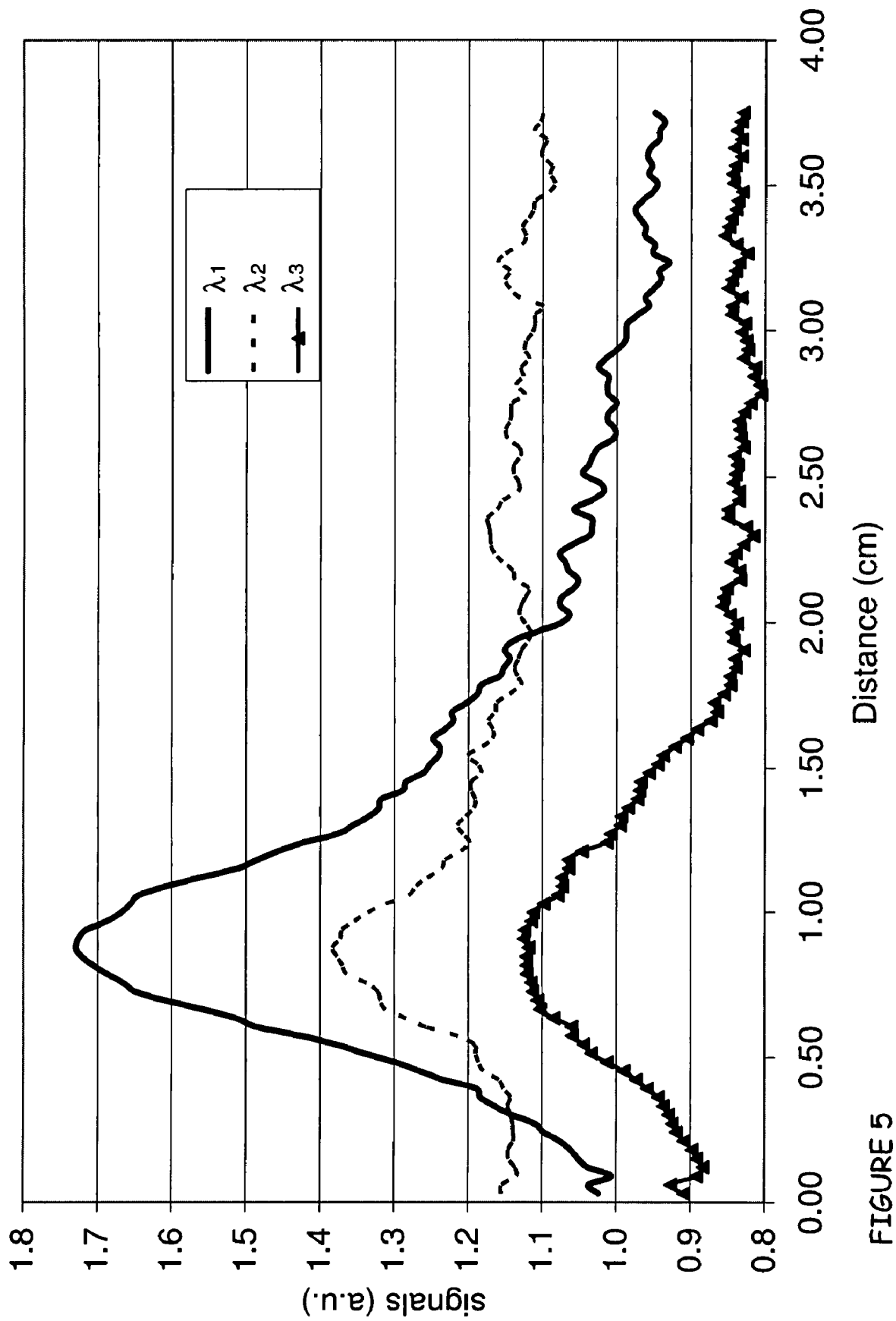
FIG. 5 shows an example of the cross correlation of a synthetic tissue model using phase modulated continuous acoustic signal for three different light wavelengths.

Referring to FIG. 5, there is exemplified a case for the phase modulation of signal $S_2$. The figure shows the amplitude of $C(\tau)$ (i.e. amplitude of cross correlation $CCA(\tau,\lambda)$), obtained for different values of delay $\tau$, as a function of distance from the acoustic transducer, where this distance equals to the product of $\tau$ by the speed of sound in the medium. Three graphs are presented, showing $CCA(\tau,\lambda)$ calculated from experimentally obtained measured data MD corresponding to a light response at three different wavelengths $\lambda^1, \lambda^2, \lambda^3$, respectively.

In this example, three different light sources, at three different wavelengths, illuminate a turbid medium, and a detection unit generates electronic signals indicative of measured data corresponding to light collected at the input port of the detector, for each wavelength used. As can be seen in the figure, the amplitudes of cross correlation signals $CCA(\tau,\lambda^1)$, $CCA(\tau,\lambda^2)$, $CCA(\tau,\lambda^3)$, or generally $CCA(\tau,\lambda^i)$, at varying distances is different for the three wavelengths. This results from the fact that the light distribution of the three wavelengths in the tissue is different, due to differences in absorption, scattering and index of refraction.

Signal $CCA(\tau,\lambda^i)$ corresponds to the acoustic distribution or pressure amplitude $PA(z)$, and to the light distribution $LD(\lambda^i)$.

$$LD(z,\lambda^i) = K * \prod_{\alpha=s,d}\left(1 + \frac{1}{\mu^i\sqrt{(\vec{r}-\vec{r}_\alpha)^2 + z^2}}\right) \quad [7]$$

$$\frac{z}{(\vec{r}-\vec{r}_\alpha)^2 + z^2}\exp\left(-\mu^i\sqrt{(\vec{r}-\vec{r}_\alpha)^2 + z^2}\right)$$

where K is a constant, $\mu^i = \sqrt{3\mu_a^i(\mu_a^i + \mu_s^i)} \cong \sqrt{3\mu_a^i\mu_s^i}$ is the effective decay rate of light in the medium, $\mu_a^i$ is the absorption coefficient and $\mu_s^i$ is the scattering coefficient at wavelength $\lambda^i$; when near infrared light is used, it can be assumed that $\mu^i \leq \sqrt{3\mu_a^i\mu_s^i}$, $\vec{r}_\alpha$ is either the vector to the source (a=s) or to the detector (a=d), and z is the direction parallel to the direction of propagation of the acoustic radiation into the medium.

For example, for a large enough distance z ($z=\tau \cdot c_s$, $c_s$ being the speed of sound in the medium) from the body surface (namely larger than the mean free path of light in the medium, and larger than the source detector separation, $\vec{r}_d - \vec{r}_s$, the light distribution $LD(z,\lambda^i)$ is proportional to $e^{-2\mu^i a}$, where $CCA(z,\lambda^i)$) is given by $CCA(z,\lambda^i) \cong PA(z)I_0^i e^{-2\mu^i z} + C_o$, where $I_0^i$ is the initial light intensity upon entry into the medium, and $C_o$ is an additive constant.

Thus, turning back to FIG. 2B, if the acoustic pressure amplitude PA(z) is known, for example by measuring it with a hydrophone in water, the light distribution $LD(z,\lambda^j)$ can be extracted by dividing PA(z) out of $CCA(z,\lambda^i)$, after eliminating $C_o$. In many practical cases, however, the pressure profile is unknown, for example when the medium consists of different layers with different acoustic impedances. Thus, there is no correspondence between measurements of the pressure profile in water or synthetic phantoms and the correct pressure profile in the measured medium. In such cases, measurements with at least two or generally N different light wavelengths can be performed, and corresponding $CCA(z,\lambda^i)$ are used to eliminate the acoustic contribution PA(z) (after eliminating $C_o$). This is implemented by dividing measured CCA $(z,\lambda^i)$ by measured $CCA(z, \lambda^j)$ for $i \neq j$, assuming that the acoustic contribution is the same for all wavelengths, which is a justifiable assumption. Thus, the ratio of the light distributions can be obtained. This ratio is important for example for determining the oxygen saturation of a tissue or blood vessel as will be explained below.

Constant $C_o$ corresponds to the noise level of the system at the measured frequency bandwidth. For example, one possible way to measure $C_o$, is to cross correlate measured data MD with a time-reversed signal $S_p(\tau - t)$. Such a correlation results in the same frequency bandwidth, but is completely uncorrelated with measured data MD. Thus, constant $C_o$ for each wavelength of light can be measured independently and eliminated from signal $CCA(z\lambda^i)$. Alternatively, $C_o$ can be eliminated by performing the measurements at two different amplitudes of acoustic radiation, and taking the difference between the two corresponding cross correlations.

In the case of a medium irradiated by three different wavelengths:

$$\frac{\tilde{I}^i}{\tilde{I}^j} = \frac{I_0^i}{I_0^j} e^{-2\Delta\mu^{ij} z} \quad [8]$$

where i; j=1; 2; 3 represent the three lasers, $\tilde{I}^i = (CCA(z, \lambda^i) - C_o)$ is the amplitude of the signal at distance z, $I_0^i$, $I_0^j$ are the input intensities of the $i^{th}$ and $j^{th}$ wavelengths respectively and $\Delta\mu^{ij} = \mu^i - \mu^j$.

Taking a logarithm of the equation above, $\Delta\mu^{ij}$ can be obtained:

$$\Delta\mu^{ij} = -\frac{1}{2}\frac{\partial}{\partial z}\ln\left[\frac{\tilde{I}^i}{\tilde{I}^j}\right] \quad [9]$$

The saturation s is related to the absorption coefficient $\mu_a^i$ by the following relation:

$$\mu_a^i = \epsilon_{Hb}^i C_{Hb} + \epsilon_{HbO}^i C_{HbO} = C_{tot}(\epsilon_{Hb}^i + (\epsilon_{HbO}^i - \epsilon_{Hb}^i)s) \quad [10]$$

where $C_{Hb}$, $C_{HbO}$ and $C_{tot}$ are the concentrations of deoxygenated hemoglobin, oxygenated hemoglobin and the total hemoglobin, respectively, s is the oxygen saturation defined as the ratio between the concentration of oxygenated hemoglobin to the total hemoglobin concentration (i.e. $s = C_{HbO}/C_{tot}$), and $\epsilon_{Hb}^i$, $\epsilon_{HbO}^j$ are the extinction coefficients at the $i^{th}$ wavelength for deoxygenated and oxygenated hemoglobin, respectively, that are known in the literature.

Thus, for any saturation s, the theoretical $\mu_a^i$ can be calculated using this equation, in order to determine the saturation at different tissue layers. The decay coefficient $\mu^i$ can be calculated for example from the graphs presented in FIG. 5. If the scattering coefficient is assumed to be the same for all three wavelengths, the absorption coefficient at each wavelength equals:

$$\mu_a^i = \frac{(\mu^i)^2}{3\mu_s},$$

and the ratio $a^{ijk}$ can be calculated by:

$$a^{ijk} = \frac{\Delta\mu^{ij}}{\Delta\mu^{ik}} = \sqrt{\frac{\epsilon_{Hb}^i - \epsilon_{Hb}^j + (\epsilon_{HbO}^i - \epsilon_{HbO}^j - \epsilon_{Hb}^i + \epsilon_{Hb}^j)s}{\epsilon_{Hb}^i - \epsilon_{Hb}^k + (\epsilon_{HbO}^i - \epsilon_{HbO}^k - \epsilon_{Hb}^i + \epsilon_{Hb}^k)s}}, \quad [11]$$

The following explains how the saturation is calculated by using measured data obtained by three lasers, and using the differences in $\Delta\mu^{12}$ and $\Delta\mu^{31}$:

The extinction coefficients are known from the literature, so that for Sat=1-100% the theoretical values for $\Delta\mu_{th} = (\Delta\mu_{th}^{12}, \Delta\mu_{th}^{31})$ can be calculated up to the multiplicative constant $\sqrt{3 \cdot \mu_s^i \cdot C_{tot}}$. The scattering coefficient $\mu_s^i = \mu_s$ is approximated to be the same for the three lasers, however it may vary with time. In order to compare the experimental value $\Delta\mu_{ex} = (\Delta\mu^{12}_{ex}, \Delta\mu^{31}_{ex})$ to the theoretical value $\Delta\mu_{th}$, the angle between the vectors in the plane that is spanned by $[\Delta\mu^{12}, \Delta\mu^{31}]$ is determined. For each experimental point there is a certain value of $\Delta\mu_{ex}$. The angle between this experimental vector and every theoretical option (corresponding to saturation values of 1%-100%) is calculated. The saturation value that corresponds to $\Delta\mu_{th}$, which has the smallest angle to $\Delta\mu_{ex}$, is the calculated saturation level. Thus, the saturation is calculated without depending on the factor $\sqrt{3 \cdot \mu_s^i \cdot C_{tot}}$.

Experimental data of the graphs presented in FIG. 5 was collected when the distance between the illumination and detection units was 3 cm. The peak intensity was obtained at about 9 mm from the skin (there is a 2-3 mm distance between the transducer face and the skin surface in this measurement). In order to map the three dimensional light distribution, different separations between the source and the detectors should be used.

Once the saturation s is determined, the total hemoglobin concentration $C_{tot}$ can be determined from measurements of the exponential decay of $CCA(z, \lambda^i)$ at the different wavelengths, using the known extinction coefficients for oxygenated and deoxygenated hemoglobin.

It should be noted that, in addition to the oxygen saturation level, other parameters of the tissue and blood composition or parameters can be determined from measurements of $CCA(z, \lambda^i)$. Moreover, the present invention provides for using determination of $\Delta\mu_{ex}$, without relying on measuring $CCA(z, \lambda^i)$, for example by using frequency domain spectroscopy or time of flight based measurements, to determine the following parameters independent of the measurement method:

For example, total Hemoglobin content $C_{tot}$ can be calculated as follows: Since the angle between the vectors $\Delta\mu_{th}$ and $\Delta\mu_{ex}$ corresponds to the calculated saturation, the multiplicative factors (i.e. $\sqrt{3 \cdot \mu_s^i \cdot C_{tot}}$) that are neglected in the theoretical calculation of $\Delta\mu_{th}$ are of no consequence to the saturation value that results from the disclosed algorithm. If there is a change in the total blood concentration, $C_{tot}$, or the scattering coefficient, $\mu_s$, without changes in the oxygen saturation level, it will be reflected by the distance of the experimental point from the origin (see Eq. [10]), but the direction of the vector from the origin to the experimental point will remain the same. Therefore, the total blood concentration can be measured by determining the distance of the experimental $\Delta\mu_{ex}$ point from the origin. Changes in the scattering coefficient can be extracted using other optical methods, such as time of flight or frequency domain spectroscopy. Consequently, independent measurements of the total blood concentration $C_{tot}$ and the scattering coefficient $\mu_s$ can be made.

Another parameter that can be determined from measurements of $CCA(z, \lambda^i)$ is blood flow. In general, the measured tissue volume contains blood vessels and capillaries. The flow of blood inside these vessels affects the properties of the measured data. The speckle correlation time is affected by the flow, there is a flow dependent Doppler shift in the acoustic waves and other effects may exist. Direct measurement of the speckle correlation time is known to correspond to blood flow velocities [G. Yu et al Journal of Biomedical Optics 2005 10:2]. Thus, the properties of $CCA(z, \lambda^i)$, such as the peak amplitude, the noise level Co and other parameters are affected by the flow. By monitoring these parameters, as a function of time, changes in the flow rates are extracted. In particular, by monitoring these changes as a function of depth, flow distribution can be determined.

Yet other measurable parameters include differences between arterial and venous contribution to the signal. In this connection, the following should be noted: General Near Infrared Spectroscopy (NIRS) measurements do not distinguish between the arterial, capillary, and venous compartments of blood circulation and thus reflect a weighted average of Hb concentrations within these different blood compartments in the region sampled. For example, in brain, the relative distribution of arterial, capillary, and venous compartments in the cerebral blood volume (CBV) is generally accepted to be approximately 20%, 10%, and 70% respectively. Using this distribution, $C_{tot}$ in the venous compartment can be isolated as follows:

$$C_{tot}=0.2[Hb]a+0.1[Hb]c+0.7[Hb]v$$

where $C_{tot}$, [Hb]a, [Hb]c, and [Hb]v are the concentrations of total Hb, arterial Hb, capillary Hb, and venous Hb, respectively. Using the assumption that the capillary concentration of Hb is the mean of arterial and venous concentrations, it is possible to determine [Hb]v, given that $C_{tot}$ can be measured and [Hb]a can be calculated from the arterial saturation $SaO_2$ using measured Hb content of arterial blood and CBV as a measure of the percentage of blood in a given tissue volume. SaO2 can be measured using a pulse oximeter. Because Hb is generated in the brain solely through the process of $O_2$ dissociation from $HbO_2$, the difference in [Hb]a and [Hb]v is identical, although opposite in sign, to the difference in $[HbO_2]a$ and $[HbO_2]v$, assuming that CBV remains constant during the measurement period.

Yet another parameter that can be determined, based on measurements of $CCA(z, \lambda^i)$, is the oxygen extraction fraction (OEF). OEF is the percentage of oxygen extracted from arterial blood in the tissue:

$$OEF\_=(arterio\text{-}venous\ O_2\ diff)/CaO_2, \quad [12]$$

where $CaO_2$, the arterial oxygen content, can be calculated from the arterial saturation (measured by a pulse oximeter for example, as explained by Brown D. W. et al. Pediatric Research Vol 54 No 6 2006 pp 861-867); and $$(arterio\text{-}venous\ O_2\ diff)=([Hb]v\_-[Hb]a)*1.39\ ml\ O_2/gHb \quad [13]$$

where [Hb]v and [Hb]a are defined above.

Therefore, as the total hemoglobin content $C_{tot}$ can be extracted as explained above, the oxygen extraction fraction in the measured tissue volume can be determined using the preferred embodiment.

Reference is now made to FIGS. 6A-6C schematically illustrating three examples, respectively, of the probe configurations according to further embodiments of the invention. In these examples the probe includes an annular acoustic transducer unit 110 and light input and output ports IP and OP such that at least one of these ports is located within an annular aperture of the acoustic transducer module. In the example of FIG. 6A, a common light guiding unit 310 is used through which fibers 105 and 106, associated with the light output and input ports OP and IP (i.e. with the lighting and detecting elements), pass. In the example of FIG. 6B, the configuration is generally similar to that of FIG. 6A, but utilizes separate light guiding units 312 and 311 located inside the transducer unit's aperture and associated with lighting and detecting elements, respectively. In the example of FIG. 6C, a light guiding unit 310 carrying an optical fiber 306 associated with light detecting element IP is located inside the transducer's aperture, and a lighting element OP is located outside the transducer unit adjacent thereto being connected to a light source or control unit via an appropriate connection 105. The location of elements corresponding to lighting elements and light detecting elements can be interchanged.

Figure 7A:
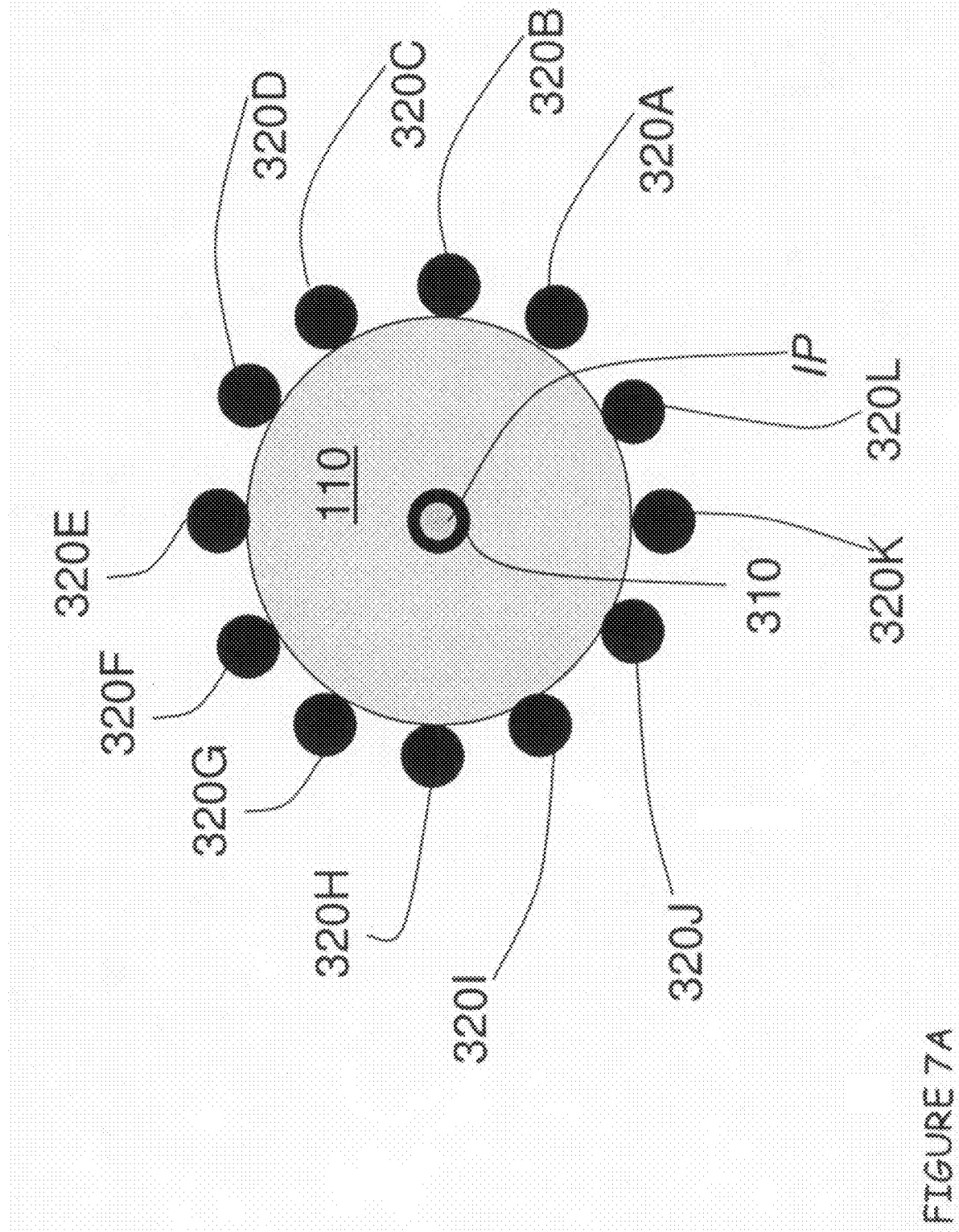
Figure 7B:
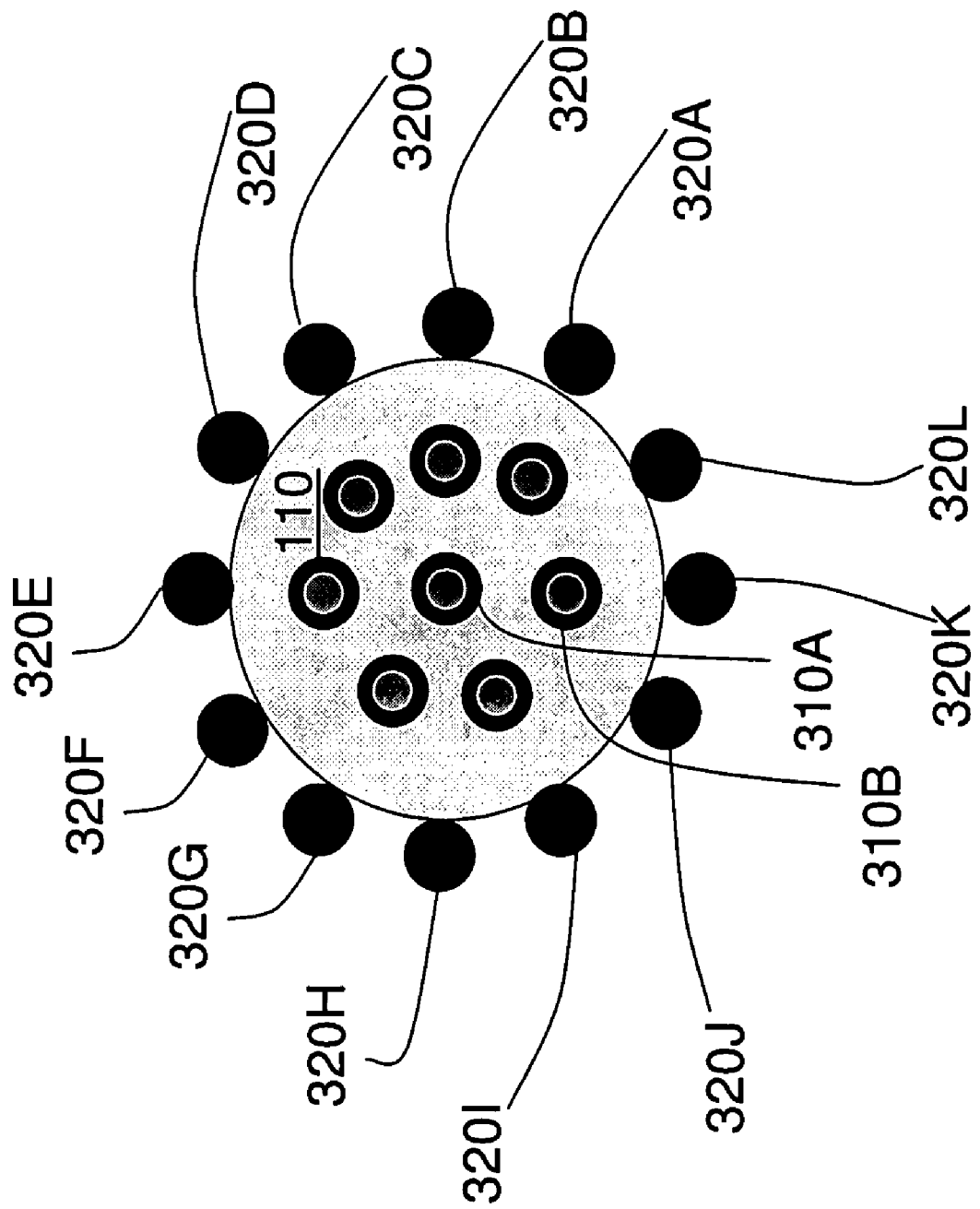

FIGS. 7A and 7B schematically illustrate two more examples, respectively, of a probe configuration according to the invention. In both of these examples, an acoustic transducer unit 110 is configured for passage therethrough of at least one light guiding unit associated with light detecting element(s), and an illumination unit includes a plurality of lighting elements located outside the transducer arrangement adjacent thereto. The lighting elements are arranged in a circular array around the light detecting element(s). In the example of FIG. 7A, a single light detecting element IP is used being located in an aperture of the transducer and associated with an appropriate light guiding unit 310 (e.g. fiber), and a circular array of twelve lighting units 320A-320L is used. In the example of FIG. 7B, an illumination unit includes eight light detecting elements are used located in corresponding spaced-apart apertures of the transducer. The light detecting elements include a central element 310A and elements 310B arranged in a circular array around element 310A. The location of elements corresponding to lighting elements and light detecting elements can be interchanged.

Figure 8A:
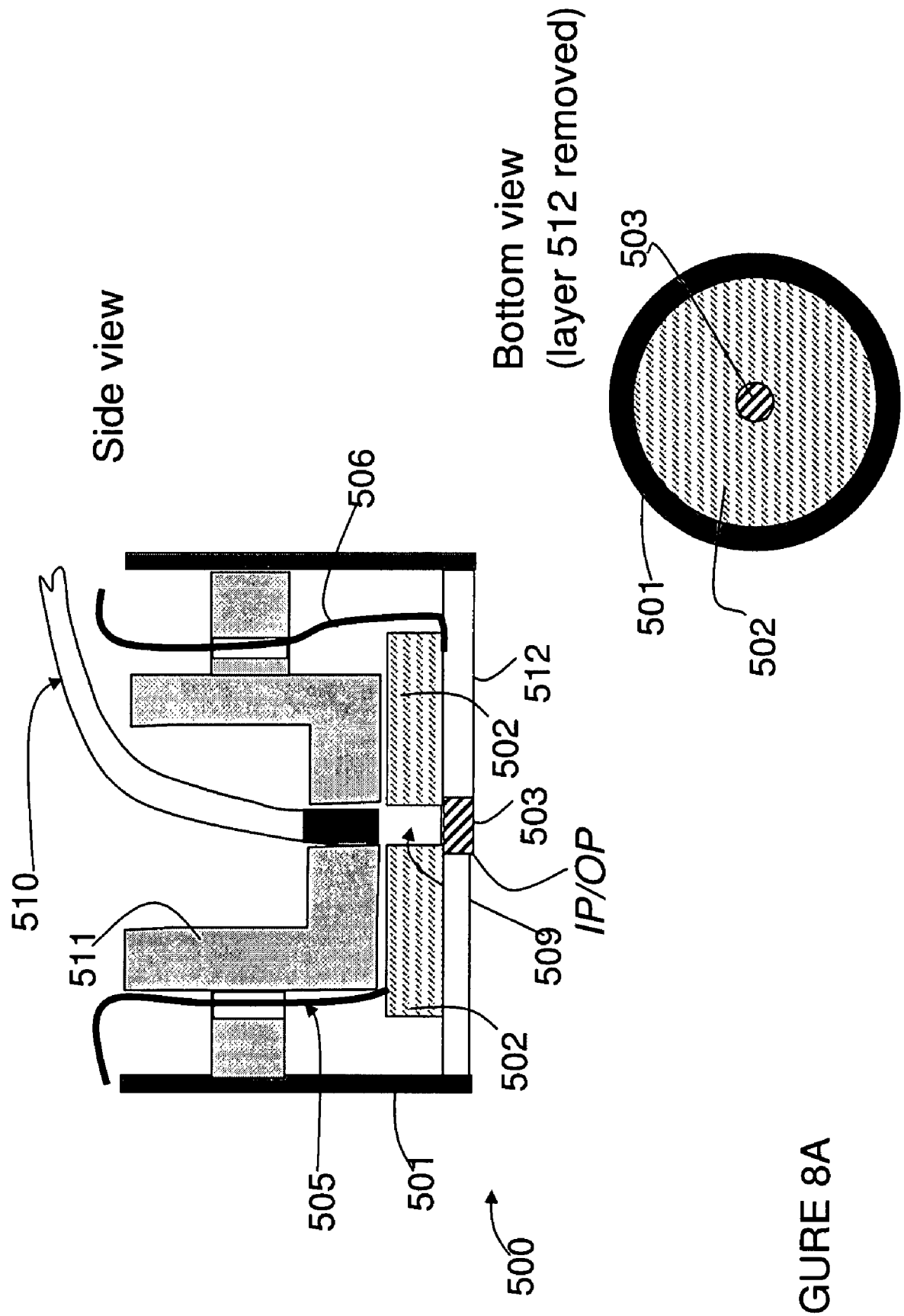
FIGS. 8A and 8B show an example of transducer's assemblies including light guides.
Figure 8B:
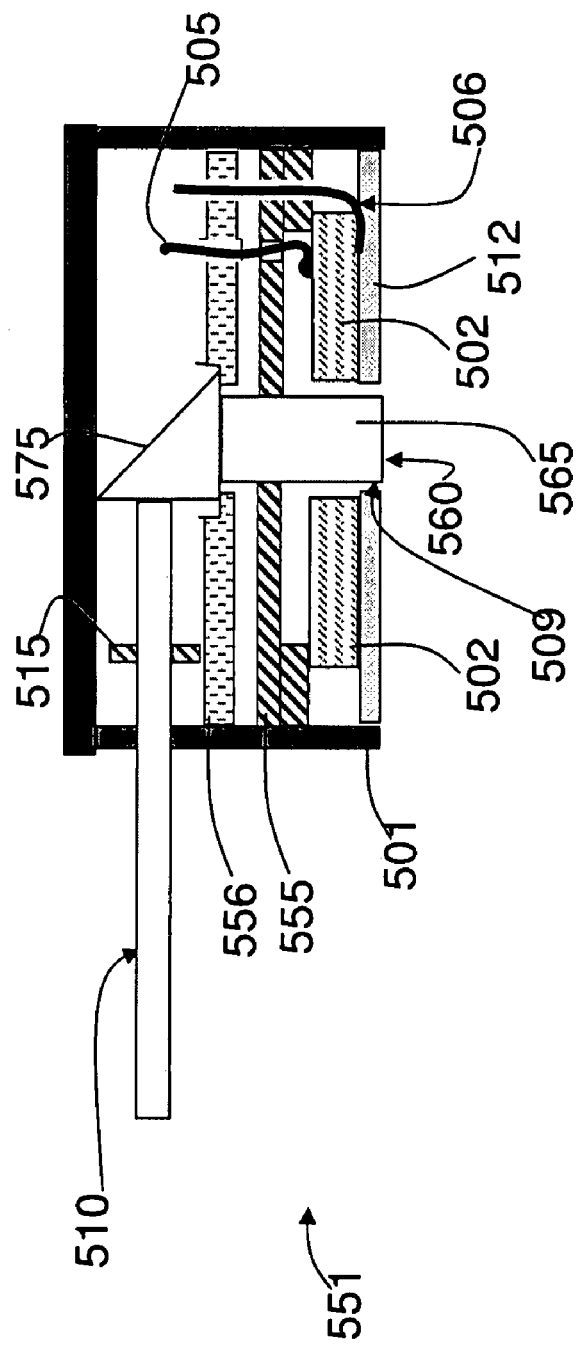

Reference is made to FIGS. 8A and 8B exemplifying the transducer's assemblies including light guides.

FIG. 8A shows a transducer's assembly 500 that includes a light guiding element in the center. The assembly may be configured such that there is no acoustic contact between the light guiding element (an optical fiber) and the piezoelectric element that generates the acoustic waves. Assembly 500 comprises a casing 501 that encapsulates piezoelectric element 502 and light guide 510. To allow for light delivery through piezoelectric element 502, the piezoelectric element 502 is formed with an optical window 509 having a diameter large enough to provide light propagation from/to light guide 510 through this optical window 509. Optical window 509 may be a physical hole, or may be a transparent opening in the piezoelectric element. Piezoelectric element 502 may also be completely transparent to light, and therefore optical window 509 may be a part of piezoelectric element 502. In addition, the optical window 509 may include a transparent optical rod that will allow light propagation through. In case the optical window 509 is a physical hole, an additional optical window 503 can also be used to seal this hole 509. Further provided is a support 511 configured to allow aligning of the optical window 509 with the aperture of light guide 510. Electric wires 505 and 506 are coupled to the two electrodes (not shown) on the piezoelectric element 502, for generating acoustic waves. These two wires are connected to cable 107 (see FIG. 1) used to deliver electrical signals from the signal generator (125 in FIG. 1).

FIG. 8B shows an assembly 551 including a casing 501 that encapsulates piezoelectric element 502 and optical guide 510. Optical guide 510 enters the casing 501 through an opening (not shown) and is supported by a support structure 515 inside the casing. Another support structure 556, positioned inside the casing, supports a prism 575. The prism is positioned such that light coupled from optical guide 510 is directed towards a further optical guide 565. This optical guide 565 is positioned inside a through hole (optical window) 509. The piezoelectric element 502 is supported by a support structure 555 that prevents acoustic coupling to the casing walls. Electric wires 505 and 506 are coupled to the two electrodes (not shown) on the piezoelectric element 502, for generating acoustic waves. Alternatively, the optical guide 510 may be input from the side its end cut at an angle to allow for the light trapped inside the fiber to reflect at a 90° angle, i.e. a side firing fiber, instead of propagating through the prism 575.

The above configurations allow for selecting the light input and output ports for use in measurements so as to provide an optimal distance between the operative input and output ports. This is associated with the following: As the distance between the light source and light detector is reduced (to ~zero), the contribution of light reflected from superficial layers to the untagged signal in the detected light is higher than in the case of larger source-detector distance. Therefore, in order to detect the tagged light from deep layers, the detection unit preferably includes an electronic filter, one of the kind that filters the low frequency signals generated in response to untagged light from the signals corresponding to tagged light (at higher frequency corresponding to the ultrasound bandwidth). Reducing the source-detector distance also improves the accuracy in calculating the optical properties of the medium, improving the determination of the desired parameter(s), e.g. calculation of the oxygen saturation level. When the source-detector distance is small, the differences in the optical paths of the shallow photons and the deep photons (that are used to calculate the optical attenuation coefficient) depend primarily on the distance traveled in the z direction (along the radiation direction towards the region of interest). Whereas for larger source-detector distance, the optical attenuation also depends on the differences in the x and y dimensions, and thus degrades the dependence on the z direction, rendering the calculations more complex.

As a result of the ultrasound beam interacting with the light, the signal that we obtain includes an integral over $\vec{r}$ of $LD(\lambda^i)$ within $V_{US}$ the volume of the ultrasound beam $$I = \int_{V_{US}} d\vec{r} \, LD(\lambda^i).$$

This integral will clearly depend on $\vec{r}_s$ and $\vec{r}_d$. The expression for the light distribution $LD(z)$ (Eq [7]) shows that its integral over $\vec{r}$ depends on the source-detector distance $r_{sd}$, such that as distance $r_{sd}$ decreases the light distribution $LD(z)$ will depend primarily on the exponential decay.

In addition, at large source-detector distances, there are many more scattering events of photons reaching the detector than for small source-detector distances. Thus, as different wavelengths are scattered differently by the tissue and cells, the difference between the optical paths of the different wavelengths increases as the source-detector distance increases. Since it was assumed above that the scattering coefficient is the same, the error in making this assumption increases as the source-detector distance increases.

Thus, the present invention provides for an effective technique for determining one or more desired parameters of a subject using an acoustic tagging of light, where acoustic radiation is generated in the form of a continuous wave, which is coded (modulated) to vary in accordance with a predetermined function of at least one parameter of the acoustic radiation which is non-periodic over a measurement time interval. The invention also provides an optimized probe configuration to obtain a required distance between the light input and output ports used in the measurements.

Those skilled in the art will readily appreciate that various modifications and changes can be applied to the embodiments of the invention as hereinbefore described without departing from its scope defined in and by the appended claims. In the method claims that follow, alphabetic characters and numerals used to designate claim steps are provided for convenience only and do not imply any particular order of performing the steps.

The invention claimed is:

1. A method for use in determining one or more parameters of a subject, said method comprising;
   (a) irradiating a region of interest of the subject with acoustic tagging radiation, the acoustic tagging radiation comprising at least one acoustic tagging beam being a coded continuous acoustic wave in the form of a predetermined function of at least one parameter of the acoustic radiation varying over time during a measurement time interval, said predetermined time function having a narrow autocorrelation;
   (b) irradiating at least a portion of the region of interest with at least one electromagnetic beam of a predetermined frequency range;
   (c) detecting an electromagnetic radiation response of said at least portion of the region of interest and generating data indicative thereof, said response comprising electromagnetic radiation tagged by the acoustic radiation, thereby enabling processing said data indicative of the detected electromagnetic radiation response, to determine at least one parameter of the subject in a region corresponding to the locations in the medium at which the electromagnetic radiation has been tagged by the acoustic radiation, and output data indicative of the at least one determined parameter.

2. The method according to claim 1, wherein said continuous acoustic wave is coded by modulating said at least one wave parameter selected from the following: phase, amplitude, frequency, frequency gradient, phase jump, duty cycle, chirp gradient.

3. The method according to claim 1, wherein said continuous acoustic wave is coded by modulating its phase.

4. The method according to claim 3, wherein the phase modulated continuous acoustic wave is generated as a sequence of pulses having equal or not values of at least one of the following parameters: duration, amplitude, frequency, frequency gradient, phase jump, duty cycle and chirp gradient.

5. The method according to claim 1, wherein said acoustic tagging beam is produced by operating an acoustic transducer with at least one coding signal in the form of an arbitrary sequence to thereby modulate output of the acoustic transducer in at least one of frequency, phase and amplitude parametric domains.

6. The method according to claim 5, wherein said arbitrary sequence is a pseudo random sequence with a narrow autocorrelation.

7. The method according to claim 5, wherein said at least one coding signal includes at least one of Barker and Golay codes.

8. The method according to claim 5, wherein said at least one coding signal includes short pulses of high amplitude and separation periods of low amplitude.

9. The method according to claim 8, wherein the separations periods are selected such that the phase of light propagating through the media during each pulse is uncorrelated to the phase of light propagating through the media during the timely adjacent pulses.

10. The method according to claim 1, comprising processing said data indicative of the detected electromagnetic response by cross-correlating said data with either said coded signal or a function of said coded signal.

11. The method according to claim 10, wherein the cross correlation is performed at different time delays from a start of the acoustic wave generation.

12. The method according to claim 11, wherein the cross correlation at each delay corresponds to intensity of the tagged light in the detected response corresponding to a distance from the acoustic transducer equal to a product of a speed of acoustic signal propagation in the subject's medium and the delay time.

13. The method according to claim 1, comprising processing the data indicative of the detected response, said processing comprising: correlating said data against an arbitrary sequence, used for modulating output of an acoustic transducer, or against a function of the arbitrary sequence, at different time delays from a start of the acoustic wave generation, and processing the correlated signal to search for a phase shift that gives best correlation for each delay.

14. The method according to claim 13, wherein said processing comprises correlating the data indicative of the detected response with a complex phasor representation of the acoustic sequence and taking an absolute value of the resulting phasor.

15. The method according to claim 1, comprising irradiating the region of interest with a plurality of the coded continuous acoustic waves.

16. The method according to claim 15, wherein the coding signals are in the form of arbitrary sequences corresponding to the coded continuous acoustic waves, respectively, having a near zero cross correlation at any time delay longer than a predetermined time delay.

17. The method according to claim 15, wherein the plurality of said continuous acoustic waves are directed towards the region of interest so as to constructively and/or destructively interfere in at least a part thereof thereby controlling the acoustic radiation power in a volume defined by said at least part of the region of interest.

18. The method according to claim 12, comprising determining optical properties of the region of interest at different distances from the acoustic transducer using the cross correlation.

19. The method according to claim 18, wherein an amplitude of the cross correlation at each delay $CCA(\tau,\lambda)$ is determined as a product of light distribution for wavelength $\lambda$ at the corresponding distance z and an amplitude of the acoustic wave $(PA(\tau))$ at said distance.

20. The method according to claim 19, comprising determining the light distribution eliminating contribution of the acoustic wave distribution to the amplitude of the cross correlation, and determining the optical properties by fitting the light distribution to an expected distribution.

21. The method according to claim 18, comprising using the cross correlation for determination of at least one of the following parameters: oxygen saturation level; total hemoglobin content; and blood flow.

22. The method according to claim 21, wherein the oxygen saturation is determined by calculating the spatial gradient of the logarithm of the ratio of two light distributions obtained by detecting the light illuminating the tissue at two different illuminating wavelengths; repeating said calculation by detecting the light illuminating the tissue at two different wavelengths, at least one wavelength being different from said two illuminating wavelengths; and determining the oxygen saturation by mapping the two calculations to known theoretical or empirical calculations of blood oxygen saturation levels.

23. The method according to claim 22, wherein said mapping is done by finding the minimal angle between the measured and theoretical vectors that correspond to said two calculations.

24. The method according to claim 22, wherein the measurement is repeated by more than two pairs of different wavelengths.

25. The method according to claim 21, wherein the blood flow is determined by monitoring at least one of the peak amplitude and noise level of the cross correlation signal for at least one wavelength of light, as a function of time, thereby determining changes in the flow rate, thereby enabling determination of the flow distribution by monitoring said changes as a function of depth.

26. The method according to claim 5, wherein said arbitrary sequence is generated using a random number generator with an essentially long period with respect to a length of a respective segment.

27. A system for use in determining one or more parameters of a subject, the system comprising: an acoustic unit configured and operable for irradiating a region of interest with acoustic tagging radiation comprising at least one acoustic tagging beam being a coded continuous acoustic wave in the form of a predetermined function of at least one parameter of the acoustic radiation varying over time during a predetermined time interval used for measurements, said predetermined function having narrow autocorrelation; an optical unit configured and operable for irradiating at least a portion of the region of interest with at least one electromagnetic beam of a predetermined frequency range, detecting an electromagnetic radiation response of said at least portion of the region of interest and generating data indicative thereof, said response comprising electromagnetic radiation tagged by the acoustic radiation, said data being indicative of the at least one parameter of the subject in a region corresponding to the locations in the medium at which the electromagnetic radiation has been tagged by the acoustic radiation.

28. The system according to claim 27, wherein the acoustic unit comprises a single acoustic port for locating it at a certain distance from the region of interest.

29. The system according to claim 27, wherein the acoustic unit comprises a plurality of spaced apart acoustic ports at different locations with respect to the region of interest.

30. The system according to claim 27, wherein the optical unit comprises a plurality of light output ports at different locations with respect to the region of interest.

31. The system according to claim 27, wherein the optical unit comprises a plurality of light input ports at different locations with respect to the region of interest.

32. The system according to claim 27, wherein the acoustic unit has an essentially annular shape, the optical unit comprising at least one light input port and at least light output port accommodated within an annular aperture of the acoustic unit.

33. The system according to claim 27, wherein the acoustic unit has at least one aperture, and the optical unit comprises at least one light input port located within said at least one aperture, and a plurality of light output ports arranged in an essentially circular array around said at least one light input port outside the acoustic unit.

34. The system according to claim 27, wherein the acoustic unit comprises a signal generator and an acoustic transducer arrangement, said signal generator being configured and operable to generate at least one coding signal in the form of an arbitrary sequence to actuate the acoustic transducer arrangement to thereby modulate output of the acoustic transducer arrangement in at least one of frequency, phase and amplitude parametric domains.

35. The system according to claim 34, wherein said arbitrary sequence is a pseudo random sequence with the narrow autocorrelation.

36. The system according to claim 34, wherein said at least one coding signal includes at least one of Barker and Golay codes.

37. The system according to claim 27, comprising a control unit configured and operable to operate the acoustic and optical units and for receiving and analyzing said data indicative of the electromagnetic radiation response to identify the tagged electromagnetic radiation and corresponding locations in the subject.

38. The system according to claim 34, comprising a control unit configured and operable to operate the signal generator and the optical unit, and for receiving and processing said data indicative of the electromagnetic radiation response to identify the tagged electromagnetic radiation and corresponding locations in the subject.

39. The system according to claim 38, wherein the control unit is configured for processing said data indicative of the detected response by cross-correlating said data with said coded signal.

40. The system according to claim 39, wherein the control unit is configured for performing said cross-correlation at different time delays from a start of the acoustic wave generation.

41. The system according to claim 40, wherein the control unit is configured for determining the cross correlation at each delay as intensity of the tagged electromagnetic radiation corresponding to a distance from the acoustic transducer equal to a product of a speed of acoustic signal propagation in the subject's medium and the delay time.

42. The system according to claim 38, wherein the control unit is configured for operating the acoustic unit for generating a plurality of said coded continuous acoustic waves.

43. The system according to claim 34, wherein the control unit is configured for operating the acoustic unit for generating a plurality of said coded continuous acoustic waves.

44. The system according to claim 43, the coding signals in the form of arbitrary sequences corresponding to the coded continuous acoustic waves, respectively, having a near zero cross correlation at any time delay longer than a predetermined time delay.

45. The system according to claim 44, wherein the control unit is configured for processing said data indicative of the detected response by cross-correlating each portion of said data corresponding to the respective one of the coded continuous acoustic waves with its respective coded signal.

46. The system according to claim 45, wherein the control unit is configured for determining the cross correlation at different time delays from a predefined time relative to the start of the acoustic wave generation.

* * * * *